United States Patent
Botta et al.

(10) Patent No.: US 10,004,702 B2
(45) Date of Patent: Jun. 26, 2018

(54) LINEAR GUANIDINE DERIVATIVES, METHODS OF PREPARATION AND USES THEREOF

(71) Applicant: LEAD DISCOVERY SIENA S.R.L., Castelnuovo Berardenga Siena (IT)

(72) Inventors: Maurizio Botta, Castelnuovo Berardenga Siena (IT); Giorgio Maccari, Castelnuovo Berardenga Siena (IT); Stefania Sanfilippo, Castelnuovo Berardenga Siena (IT); Filomena De Luca, Castelnuovo Berardenga Siena (IT); Jean-Denis Docquier, Castelnuovo Berardenga Siena (IT); Davide Deodato, Castelnuovo Berardenga Siena (IT)

(73) Assignee: LEAD DISCOVERY SIENA S.R.L., Castelnuovo Berardenga Siena (IT)

(*) Notice: Subject to any disclaimer, the term of this patent is extended or adjusted under 35 U.S.C. 154(b) by 0 days. days.

(21) Appl. No.: 15/517,764

(22) PCT Filed: Oct. 9, 2015

(86) PCT No.: PCT/EP2015/073467
§ 371 (c)(1),
(2) Date: Apr. 7, 2017

(87) PCT Pub. No.: WO2016/055644
PCT Pub. Date: Apr. 14, 2016

(65) Prior Publication Data
US 2017/0304235 A1    Oct. 26, 2017

(30) Foreign Application Priority Data
Oct. 10, 2014 (IT) .................. RM2014A0580

(51) Int. Cl.
*A61K 31/155* (2006.01)
*C07C 279/12* (2006.01)
(Continued)

(52) U.S. Cl.
CPC ............ *A61K 31/155* (2013.01); *A61K 31/17* (2013.01); *A61K 45/06* (2013.01); *C07C 279/04* (2013.01);
(Continued)

(58) Field of Classification Search
None
See application file for complete search history.

(56) References Cited

U.S. PATENT DOCUMENTS

| 3,499,927 A | 3/1970 | Badcock et al. |
| 2005/0222064 A1* | 10/2005 | Vargeese ............ A61K 49/0008 514/44 A |

FOREIGN PATENT DOCUMENTS

| EP | 2520605 A1 | 11/2012 |
| GB | 1095902 A | 12/1967 |

(Continued)

OTHER PUBLICATIONS

Maccari ("Synthesis of linear and cyclic guazatine derivatives endowed with antibacterial activity" Bioorganic and Medicinal Chemistry Letters, 24, 2014, p. 5525-5529).*

(Continued)

*Primary Examiner* — Jafar Parsa
*Assistant Examiner* — Amy C Bonaparte
(74) *Attorney, Agent, or Firm* — Lucas & Mercanti, LLP

(57) ABSTRACT

The present invention relates to linear guanidine derivatives, methods of preparation, uses and pharmaceutical compositions thereof. The compounds of Formulas 1 or 2 exhibit high antimicrobial activity against Gram positive and Gram negative bacteria.

20 Claims, 1 Drawing Sheet

(51) Int. Cl.
  *C07C 279/24* (2006.01)
  *C08K 5/31* (2006.01)
  *C07C 279/04* (2006.01)
  *A61K 45/06* (2006.01)
  *A61K 31/17* (2006.01)
(52) U.S. Cl.
  CPC .......... *C07C 279/12* (2013.01); *C07C 279/24* (2013.01); *C08K 5/31* (2013.01); *C07C 2601/02* (2017.05)

(56) References Cited

FOREIGN PATENT DOCUMENTS

| WO | 2006118283 | A1 | 11/2006 |
| WO | 2008029810 | A1 | 3/2008 |
| WO | 2009113033 | A2 | 9/2009 |

OTHER PUBLICATIONS

Aissaoui ("Novel Cationic Lipids Incorporating an acid-Sensitive Acylhydrazone Linker: Synthesis and Transfection Properties" J. Med. Chem. 47, 2004, 5210-5223).*

Manetti ("Synthesis of New Linear Guanidines and Macrocylic Amidinourea Derivatives Endowed with High Antifungal Activity against *Candida* spp. and *Aspergillus* spp." J. Med. Chem. 2009, 52, p. 7376-7379).*

Manetti ("Synthesis and Biological Evaluation of Guanidino Compounds Endowed with Subnanomolar Affinity as Competitive Inhibitors or Maize Polyamine Oxidase" J. Med. Chem. 2009, 52, p. 4774-4785).*

Pallan ("DNA Triple Helix Stabilization by Bisguanidinyl Analogues of Biogenic Polyamines" Biochemical and Biophysical Research Communications, 222, 1996, p. 416-420).*

Raffi ("Efficient Synthesis of Iminoctadine, a Potent Antifungal Agent and Polyamine Oxidase Inhibitor (PAO)" Synthesis, 2007, 19, p. 3013-3016).*

Hanessian ("Tobramycin analogues with C-5 aminoalkyl ether chains intended to mimic rings III and IV of paromomycin" Tetrahedron, 2003, 59, p. 983-993).*

International Search Report and Written Opinion for International Application No. PCT/EP2015/073467 (12 Pages) (dated Dec. 17, 2015).

* cited by examiner

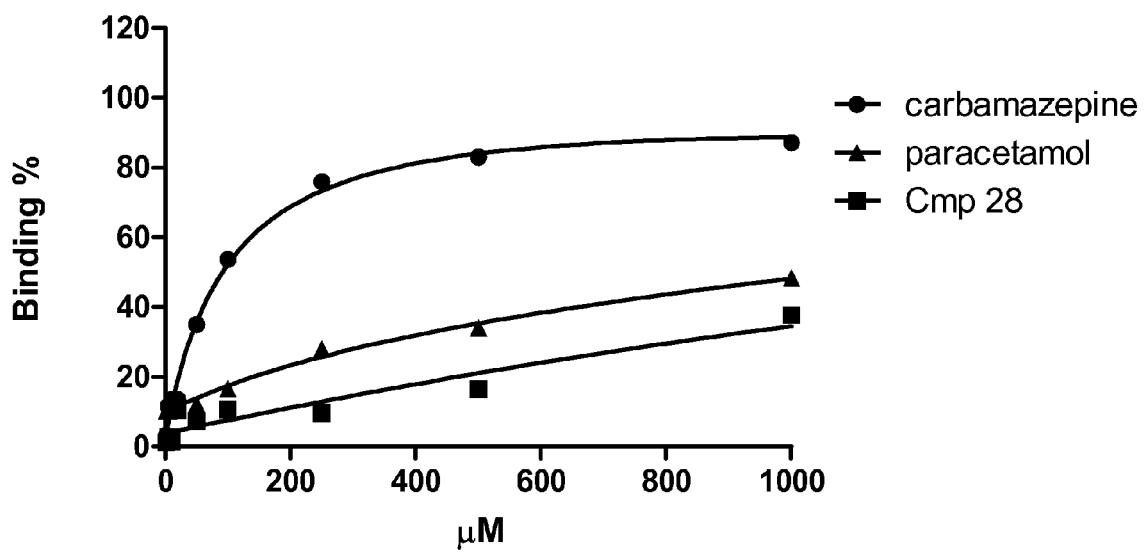

LINEAR GUANIDINE DERIVATIVES, METHODS OF PREPARATION AND USES THEREOF

CROSS-REFERENCE TO RELATED APPLICATIONS

This application is a 371 of PCT/EP2015/073467, filed Oct. 9, 2015, which claims the benefit of Italian Patent Application No. RM2014A000580, filed Oct. 10, 2014.

FIELD OF THE INVENTION

The present invention relates to linear guanidine derivatives, methods of preparation, uses and pharmaceutical compositions thereof.

BACKGROUND OF THE INVENTION

Bacterial resistance to currently available antibiotics is becoming increasingly frequent in both the hospital setting and the community. Multi-drug or even pan-drug resistance, i.e. resistance to nearly all available antibiotic classes (e.g. beta-lactams, quinolones, tetracyclines, glycopeptides and macrolides), is rapidly emerging in clinically relevant pathogens. This important clinical problem, together with the lack of investment in the discovery and development of new antibiotic treatments active on multi-drug resistant pathogens, especially Gram-negative bacteria, thus represents a relevant Public Health issue and medical need [1].

The prevalence and severity of antibiotic resistance (AR) is becoming evident worldwide and is associated with increased morbidity and mortality of infectious diseases, thus creating a huge socio-economic burden on Public Healthcare systems [1], [2].

Then, there is the need for compounds endowed with activity against both Gram-negative and Gram-positive bacteria.

Documents U.S. Pat. No. 3,499,927, WO2008/029810 and WO2006/118283 relates to guanidine derivatives of polyalkylene polyamines useful against bacteria infecting humans or against plant pathogenic fungi.

Manetti et al.[3] disclose guanidine compounds having affinity as competitive inhibitors of maize polyamine oxidase. Such compounds are interesting to inhibit cell proliferation, in particular in tumor cell lines.

The document WO2009/113033 discloses linear and cyclic guanidine derivatives for use as anti-infectious agents.

SUMMARY OF THE INVENTION

During studies on antifungal compounds, the authors have found that some linear guanidine derivatives are endowed with a good activity against both Gram-negative and Gram-positive bacteria.

The present invention concerns novel linear guanidine derivatives of different polyamines. The authors have synthesized a new series of oligomeric guanilated polyamines.

These compounds have been tested against 16 bacterial species. Surprisingly the compounds object of the present invention were found i) to possess an excellent antibacterial activity against most of the ESKAPE bacteria (*Enterococci, Staphylococci, Klebsiella* spp., *Acinetobacter* spp., *Pseudomonas* spp. and *Enterobacter* spp.) and ii) to possess an excellent antibacterial activity against antibiotic-resistant clinical isolates of the aforementioned organisms showing multi-drug resistance profiles.

The present invention provides a compound of general formula 1:

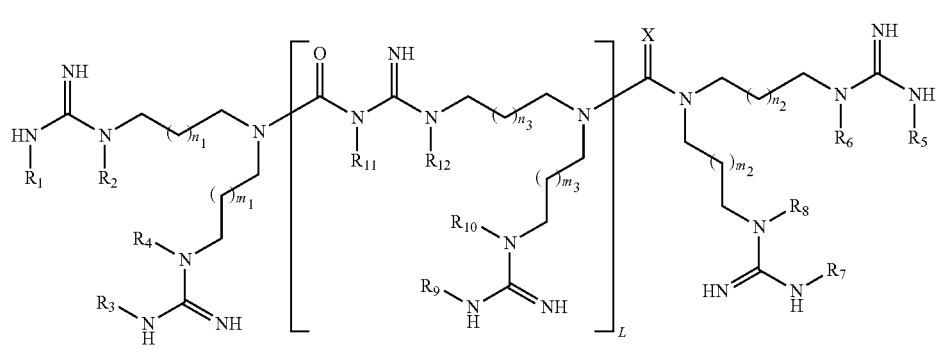

or a pharmaceutical acceptable salt, hydrate or solvate thereof;

wherein:

$R_1$, $R_3$, $R_5$, $R_7$, $R_9$ and $R_{11}$ are the same or different groups, selected between H, methyl, ethyl, propyl, prop-2-ynyl, but-2-enyl, 2-methylprop-2-enyl, 3-methylbut-2-enyl, phenyl, benzyl, dimethylphenyl, cyclopropylmethyl, cyclobutylmethyl, cyclopentylmethyl, cyclohexylmethyl, acetyl, propanoyl, N-alkyl-carbamoyl, N-alkyl-thiocarbamoyl, N-alkyl-carbamimidoyl or saturated linear or branched $C_{1-10}$ alkyl;

$R_2$, $R_4$, $R_6$, $R_8$, $R_{10}$ and $R_{12}$ are the same or different groups, selected between H, methyl, ethyl, or saturated linear or branched $C_{1-5}$ alkyl;

X is O or S;

L is a number ranging from 0 to 2;

$n_1$, $n_2$ and $n_3$ can be the same or different and are numbers ranging from 2 to 10;

$m_1$, $m_2$ and $m_3$ can be the same or different and are numbers ranging from 2 to 10;

Preferably, L=0. Still preferably $n_1=n_2=m_1=m_2=6$.

In a preferred embodiment $R_1$ and/or $R_5$ is cyclopropylmethyl or $R_1$ and/or $R_5$ is ethyl, benzyl, propargyl or but-2-enyl.

Preferably the compound is selected from the group consisting of:

1,3-bis(6-(3-(cyclopropylmethyl)guanidino)hexyl)-1,3-bis(6-guanidinohexyl)urea (31);

1,3-bis(8-(3-(cyclopropylmethyl)guanidino)octyl)-1,3-bis(8-guanidinooctyl)urea (28);

1,3-bis(8-(3-(cyclopropylmethyl)guanidino)octyl)-1-(8-guanidinooctyl)-3-(8-((3-(8-((8-(3-(cyclopropylmethyl))guanidinooctyl)amino)octyl)carbamoyl)guanidino)octyl)urea (32);

1,3-bis(8-(3-(ethyl)guanidino)octyl)-1,3-bis(8-guanidinooctyl)urea;

1,3-bis(8-(3-(buten-2-yl)guanidino)octyl)-1,3-bis(8-guanidinooctyl)urea;

1,3-bis(8-(3-(benzyl)guanidino)octyl)-1,3-bis(8-guanidinooctyl)urea;

1,3-bis(8-(3-(propargyl)guanidino)octyl)-1,3-bis(8-guanidinooctyl)urea;

1,3-bis(9-(3-(cyclopropylmethyl)guanidino)nonyl)-1,3-bis(9-guanidinononyl)urea;

1,3-bis(9-(3-(ethyl)guanidino)nonyl)-1,3-bis(9-guanidinononyl)urea;

1,3-bis(9-(3-(buten-2-yl)guanidino)nonyl)-1,3-bis(9-guanidinononyl)urea;

1,3-bis(9-(3-(benzyl)guanidino)nonyl)-1,3-bis(9-guanidinononyl)urea;

1,3-bis(9-(3-(propargyl)guanidino)nonyl)-1,3-bis(9-guanidinononyl)urea;

1,3-bis(10-(3-(cyclopropylmethyl)guanidino)decyl)-1,3-bis(10-guanidinodecyl)urea;

1,3-bis(10-(3-(ethyl)guanidino)decyl)-1,3-bis(10-guanidinodecyl)urea;

1,3-bis(10-(3-(buten-2-yl)guanidino)decyl)-1,3-bis(10-guanidinodecyl)urea;

1,3-bis(10-(3-(benzyl)guanidino)decyl)-1,3-bis(10-guanidinodecyl)urea;

1,3-bis(10-(3-(propargyl)guanidino)decyl)-1,3-bis(10-guanidinodecyl)urea;

The invention further provides a compound having the general formula 2:

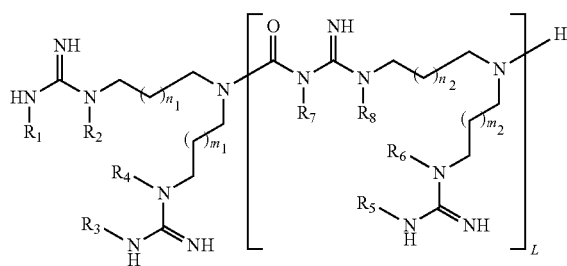

or a pharmaceutical acceptable salt, hydrate or solvate thereof;
wherein:

$R_1$, $R_3$, $R_5$, and $R_7$, are the same or different groups, selected between H, methyl, ethyl, propyl, prop-2-ynyl, but-2-enyl, 2-methylprop-2-enyl, 3-methylbut-2-enyl, phenyl, benzyl, dimethylphenyl, cyclopropylmethyl, cyclobutylmethyl, cyclopentylmethyl, cyclohexylmethyl, acetyl, propanoyl, N-alkyl-carbamoyl, N-alkyl-thiocarbamoyl, N-alkyl-carbamimidoyl or saturated linear or branched $C_{1-10}$ alkyl;

$R_2$, $R_4$, $R_6$, and $R_8$, are the same or different groups, selected between H, methyl, ethyl, or saturated linear or branched $C_{1-5}$ alkyl L is a number ranging from 1 to 3;

$n_1$ and $n_2$ can be the same or different and are numbers ranging from 2 to 10;

$m_1$ and $m_2$ can be the same or different and are numbers ranging from 2 to 10.

Preferably wherein L=1. Still preferably $R_1$ and/or $R_5$ is cyclopropylmethyl.

Yet preferably the compound is selected from the group consisting of:

1-(6-carbamimidamidohexyl)-1-[6-[[N-(cyclopropylmethyl)carbamimidoyl]amino]hexyl]-3-[N-[6-[6-[[N (cyclopropylmethyl)carbamimidoyl]amino]hexylamino]hexyl]carbamimidoyl]urea (33);

1-(8-carbamimidamidooctyl)-1-[8-[[N-(cyclopropylmethyl)carbamimidoyl]amino]octyl]-3-[N-[8-[8-[[N-(cyclopropylmethyl)carbamimidoyl]amino]octylamino]octyl]carbamimidoyl]urea (30);

1-(6-carbamimidamidohexyl)-1-[6-[[N-(cyclopropylmethyl)carbamimidoyl]amino]hexyl]-3-[N-[6-[6-[[N-(cyclopropylmethyl)carbamimidoyl]amino]hexyl-[[N-[6-[6-[[N-(cyclopropylmethyl)carbamimidoyl]amino]hexylamino]hexyl]carbamimidoyl]carbamoyl]amino]hexyl]carbamimidoyl]urea (34);

1-(8-carbamimidamidooctyl)-1-[8-[[N-(cyclopropylmethyl)carbamimidoyl]amino]octyl]-3-[N-[8-[8-[[N-(cyclopropylmethyl)carbamimidoyl]amino]octyl-[[N-[8-[8-[[N-(cyclopropylmethyl)carbamimidoyl]amino]octylamino]octyl]carbamimidoyl]carbamoyl]amino]octyl]carbamimidoyl]urea (35);

More preferably the compound of formula 1 or 2 is for medical use, preferably for use in the treatment of a bacterial infection.

In a preferred embodiment the bacteria is Gram-positive or Gram-negative.

Preferably the bacteria is selected from the group of: *Enterococci, Staphylococci, Klebsiella* spp., *Acinetobacter* spp., *Pseudomonas* spp., *Enterobacter* spp., *Achromobacter* spp., *Aeromonas* spp., *Alcaligenes* spp., *Burkholderia cepacia, Chryseobacterium meningosepticum, Escherichia coli, Stenotrophomonas maltophilia* and *Bacillus subtilis*.

Preferably the bacteria is resistant to at least one antibiotic/antibacterial agent.

The invention also provides a pharmaceutical composition comprising at least one compound of formula 1 or 2 or a pharmaceutical acceptable salt or solvate thereof and acceptable carriers, excipients or diluents.

Preferably the pharmaceutical composition is for use in the treatment of a bacterial infection.

Still preferably the pharmaceutical composition further comprises at least one other therapeutic agent, preferably an antibacterial agent.

The invention also provides a process for the preparation of a compound of formula 1 as defined above comprising the steps of:

Scheme 1.
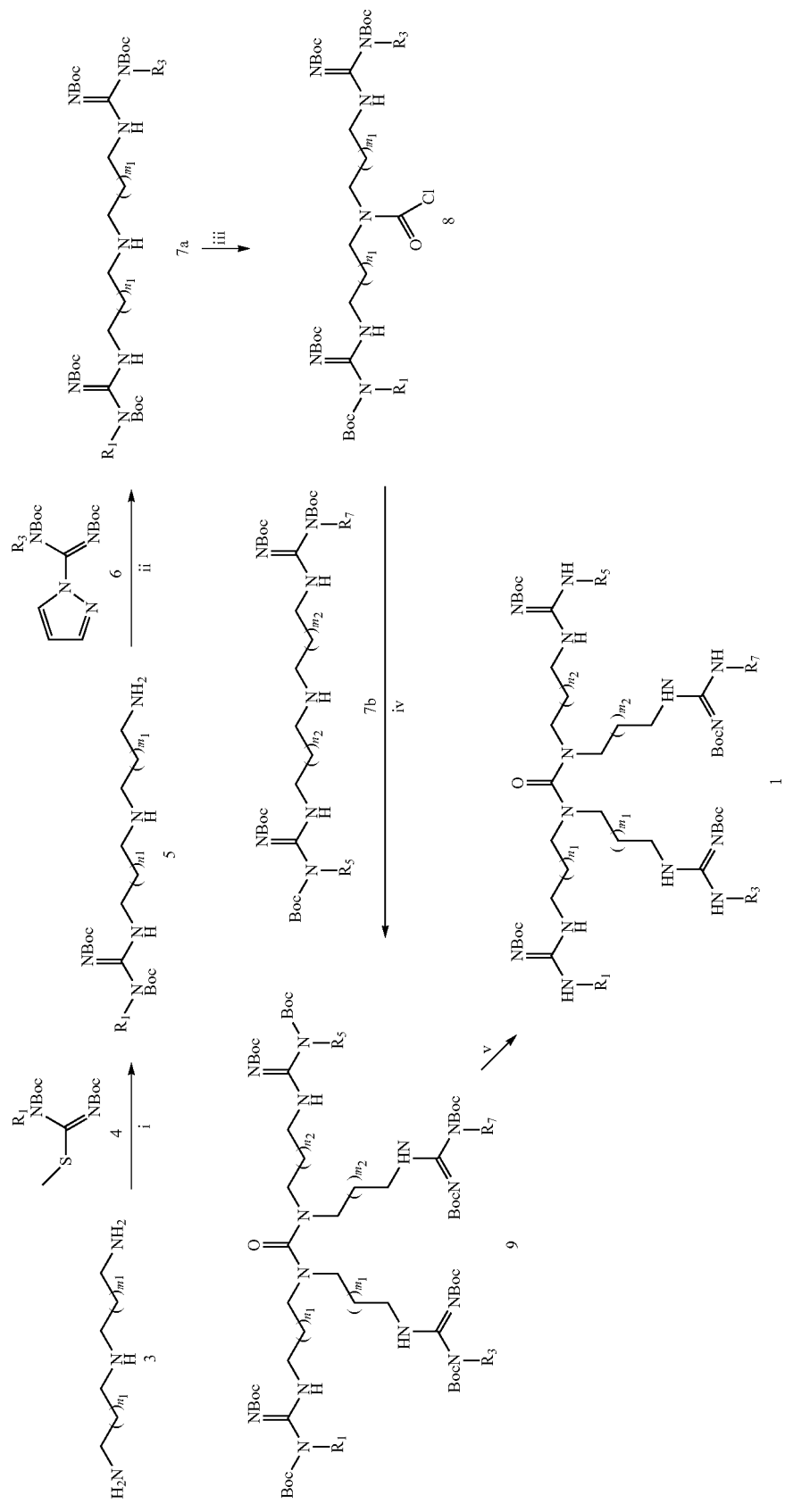
Reagents and conditions: (i) DIPEA, CH₃CN/MeOH, 50° C., 12-48 h (ii) DIPEA, THF, 50° C., 12-48 h (iii) Triphosgene, DIPEA, THF, 0° C., 10 min; (iv) DIPEA, NaI, DCM, 40° C., 48 h; (v) TFA, DCM 8-24 h. In the scheme R₁, R₃, R₅, R₇, n₁, n₂, m₁ and m₂ are defined above The invention provides a process for the preparation of a compound of formula 2 as defined above comprising the steps of:

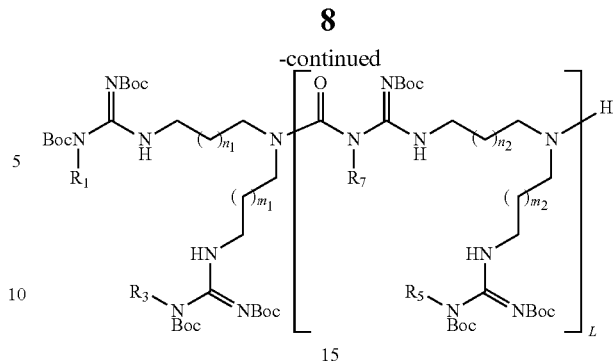

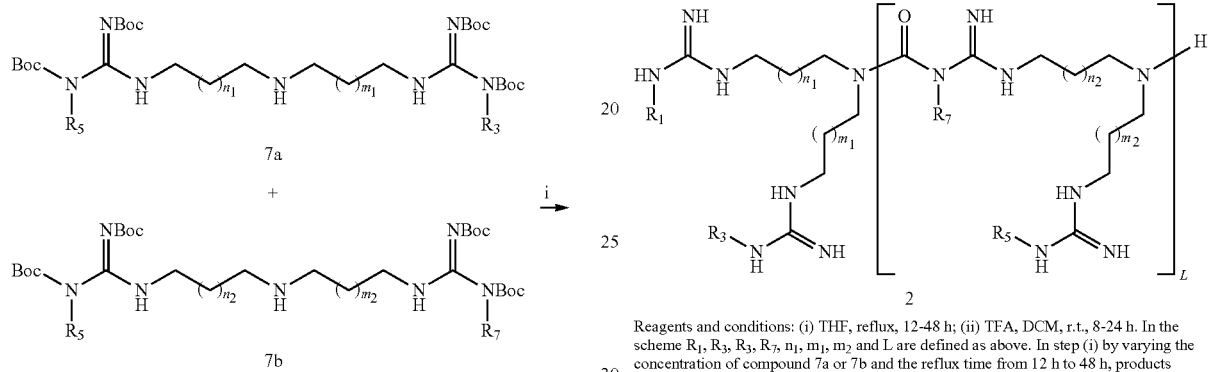

Reagents and conditions: (i) THF, reflux, 12-48 h; (ii) TFA, DCM, r.t., 8-24 h. In the scheme $R_1$, $R_3$, $R_3$, $R_7$, $n_1$, $m_1$, $m_2$ and L are defined as above. In step (i) by varying the concentration of compound 7a or 7b and the reflux time from 12 h to 48 h, products with an increasing number of L units can be synthesized and the reaction's status can be monitored through mass spectrometry.

The invention further provides a process for the preparation of an intermediate of formula 7a or 7b comprising the steps of:

Scheme 2. Alternative synthesis of compound 7a or 7b:

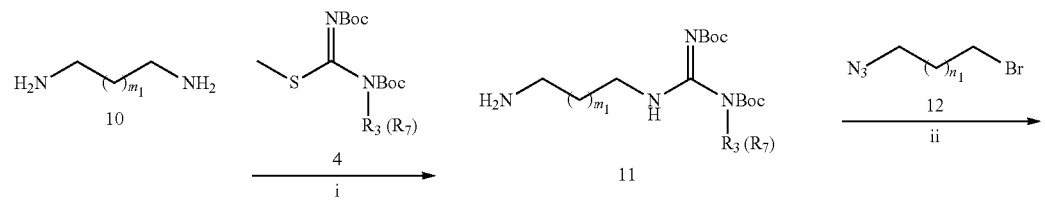

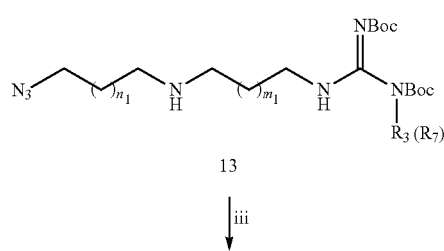

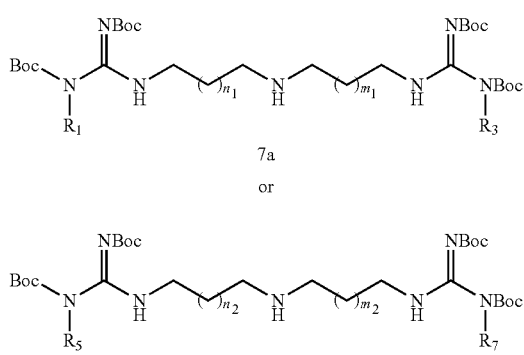

7a or

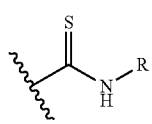

7b

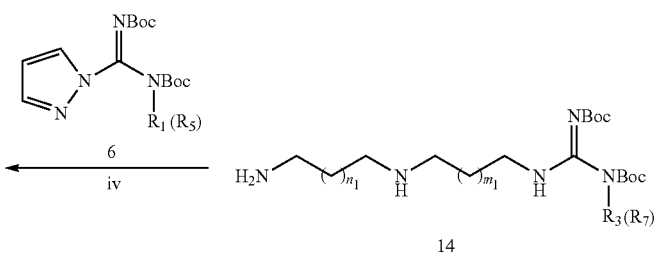

14

Reagents and conditions. (i) DIPEA, CH$_3$CN/MeOH, 50° C., 12-48 h; (ii) CsOH*H$_2$O, molecular sieves, DMF, r.t. 12 h; (iii) PPh$_3$, H$_2$O, THF, r.t., 12 h (iv) DIPEA, THF, 50° C., 12-48 h. In the scheme R$_1$, R$_3$, n$_1$, and m$_1$ are defined as above.

In the present invention, the term "alkyl" refers to a straight or branched hydrocarbon chain radical, consisting solely of carbon and hydrogen atoms. Representatives of said alkyl group include C$_{1-10}$ alkyl which refers to a straight or branched hydrocarbon chain, consisting solely of carbon and hydrogen atoms, having from one to 10 carbon atoms; preferably C$_{1-6}$ alkyl which refers to a straight or branched hydrocarbon chain, consisting solely of carbon and hydrogen atoms, having from one to six carbon atoms such as methyl, ethyl, n-propyl, isopropyl, butyl, sec-butyl, tert-butyl, pentyl, isopentyl, tert-pentyl, hexyl; more preferably C$_{1-4}$ alkyl which refers to a straight or branched hydrocarbon chain, consisting solely of carbon and hydrogen atoms, having from one to four carbon atoms, such as methyl, ethyl, n-propyl, isopropyl, butyl, sec-butyl, tert-butyl; even more preferably C$_{1-2}$ alkyl which refers to a straight or branched hydrocarbon chain, consisting solely of carbon and hydrogen atoms, having from one to two carbon atoms, such as methyl, ethyl. Suitable examples of said alkyl include but are not limited to methyl, ethyl, n-propyl, isopropyl, butyl, sec-butyl, tert-butyl, pentyl, isopentyl, tert-pentyl, hexyl, heptyl, octyl, nonyl, decanyl, hexadecanyl, eicosanyl.

The term "N-alkyl-carbamoyl" refers to:

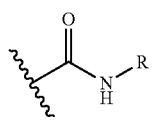

Wherein R is alkyl and the alkyl is as defined herein above. Suitable examples of "N-alkyl-carbamoyl" include but are not limited to N-methyl-carbamoyl, N-ethyl-carbamoyl, N-tert-butyl-carbamoyl, N-propan-2-ylcarbamoyl, N-propylcarbamoyl.

The term "N-alkyl-thiocarbamoyl" refers to:

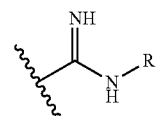

Wherein R is alkyl and the alkyl is as defined herein above. Suitable examples of "N-alkyl-thiocarbamoyl" include but are not limited to N-methyl-thiocarbamoyl, N-ethyl-thiocarbamoyl, N-tert-butyl-thiocarbamoyl, N-propan-2-ylthiocarbamoyl, N-propylthiocarbamoyl.

The term "N-alkyl-carbamimidoyl" refers to:

Wherein R is alkyl and the alkyl is as defined herein above. Suitable examples of "N-alkyl-carbamimidoyl" include but are not limited to N-methyl-carbamimidoyl, N-ethyl-carbamimidoyl, N-tert-butyl-carbamimidoyl, N-propan-2-ylcarbamimidoyl, N-propylcarbamimidoyl.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., —R$_1$, —R$_2$, —R$_3$, —R$_4$, —R$_5$, —R$_6$, —R$_7$, —R$_8$) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to compounds of formula 1 or 2, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer(s) or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., C1-7alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —OCH$_3$, is not to be construed as a reference to its structural isomer, a hydroxy methyl group, —CH$_2$OH. Similarly, a reference to ortho-chlorophenyl is not to be construed as a reference to its structural isomer, meta-chlorophenyl. The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

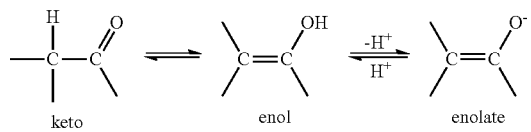

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," J. Pharm. Sci. Vol. 66, pp. 1-19.

For example, if the compound is anionic, or has a functional group which may be anionic (e.g., —COOH may be —COO$^−$), then a salt may be formed with a suitable cation.

Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$. If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, (auric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Examples of some preferred salts suitable for amines (such as the Compounds of formula 1 or 2 described herein) include: chloride, sulfate, bromide, mesylate, maleate, citrate, tartrate, phosphate, acetate, and iodide. An especially preferred salt may be the maleate salt (since perhexiline itself it currently used in therapy as the maleate salt). Unless otherwise specified, a reference to a particular compound also includes salt forms thereof.

Because of their potential use in medicine, the salts of the compounds of formula 1 and 2 are preferably pharmaceutically acceptable. Suitable pharmaceutically acceptable salts comprise conventional non-toxic salts obtained by salification of a compound of formula 1 and 2 with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see [5],[6],[7]. Other salts, which are not pharmaceutically acceptable, for example the trifluoroacetate salt, may be useful in the preparation of compounds of this invention and these form a further aspect of the invention.

Solvates and Hydrates It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc. Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, an amine group may be protected, for example, as an amide (—NRCO—R) or a urethane (—NRCO—OR), for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N-0.).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

Compositions

One aspect of the present invention pertains to a composition (e.g., a pharmaceutical composition) comprising a compound of formula 1 or 2, as described herein, and a pharmaceutically acceptable carrier, diluent, or excipient.

In one embodiment, the composition further comprises one or more (e.g., 1, 2, 3, 4) additional therapeutic agents, as described herein. Another aspect of the present invention pertains to a method of preparing a composition (e.g., a pharmaceutical composition) comprising admixing a compound of formula 1 or 2, as described herein, and a pharmaceutically acceptable carrier, diluent, or excipient.

Another aspect of the present invention pertains to a method of preparing a composition (e.g., a pharmaceutical composition) comprising admixing a compound of formula 1 or 2, as described herein; one or more (e.g., 1, 2, 3, 4) additional therapeutic agents, as described herein; and a pharmaceutically acceptable carrier, diluent, or excipient.

Uses

The compounds of formula 1 or 2, as described herein, are useful, for example, in the treatment of disorders (e.g., diseases) including, for example, those which are known to be treated with, or known to be treatable with antibacterial agents, including, for example, the disorders (e.g., diseases) described herein.

In one embodiment, the compound of formula 1 or 2 is provided in the form of a pharmaceutically acceptable composition.

Use in Methods of Therapy

Another aspect of the present invention pertains to a compound of formula 1 or 2, as described herein, for use in a method of treatment of the human or animal body by therapy, for example, for use a method of treatment of a disorder (e.g., a disease) as described herein.

Another aspect of the present invention pertains to a compound of formula 1 or 2, as described herein, in combination with one or more (e.g., 1, 2, 3, 4) additional therapeutic agents, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of compound of formula 1 or 2, as described herein, in the manufacture of a medicament for treatment, for example, treatment of a disorder (e.g., a disease) as described herein. In one embodiment, the medicament comprises the compound of formula 1 or 2.

Another aspect of the present invention pertains to use of a compound of formula 1 or 2, as described herein, and one or more (e.g., 1, 2, 3, 4) additional therapeutic agents, as described herein, in the manufacture of a medicament for treatment, for example, treatment of a disorder (e.g., a disease) as described herein.

In one embodiment, the medicament comprises the compound of formula 1 or 2 and the one or more (e.g., 1, 2, 3, 4) additional therapeutic agents.

Methods of Treatment

Another aspect of the present invention pertains to a method of treatment, for example, of a disorder (e.g., a disease) as described herein, comprising administering to a patient in need of treatment a therapeutically effective amount of compound of formula 1 or 2, as described herein, preferably in the form of a pharmaceutical composition. Another aspect of the present invention pertains to a method of treatment, for example, of a disorder (e.g., a disease) as described herein, comprising administering to a patient in need of treatment a therapeutically effective amount of a compound of formula 1 or 2, as described herein, preferably in the form of a pharmaceutical composition, and one or more (e.g., 1, 2, 3, 4) additional therapeutic agents, as described herein, preferably in the form of a pharmaceutical composition.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment".

For example, treatment of a bacterial infection includes the prophylaxis of a bacterial infection, reducing the incidence of a bacterial infection, reducing the severity of a bacterial infection, alleviating the symptoms of a bacterial infection, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents, for example, anti-bacterial agents, etc. Examples of treatments and therapies include, but are not limited to, chemotherapy (the administration of active agents, including, e.g., drugs, antibodies, prodrugs (e.g., as in photodynamic therapy, GDEPT, ADEPT, etc.); surgery; radiation therapy; photodynamic therapy; gene therapy; and controlled diets. One aspect of the present invention pertains to a compound as described herein, in combination with one or more additional therapeutic agents, as described below.

The particular combination would be at the discretion of the physician who would select dosages using his common general knowledge and dosing regimens known to a skilled practitioner. The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Additional Therapeutic Agents for Use in Combination Therapy

Known drugs which are used in combination with antibacterial drugs may also be used in combination therapy with the compound of formula 1 or 2 as described herein. Preferred antibacterial agents from the beta-lactam class include, for example, ceftazidime, cefpirome, cefepime, cefoperazone, imipenem, meropenem, piperacillin, mezlocillin, ticarcillin, the combination of piperacillin and tazobactam, the combination of ticarcillin and clavulanic acid, and BMS-180680 (Bristol Myers and Squibb) including their pharmaceutically acceptable salts. Preferred agents from the quinolone class include, for example, norfloxacin, ciprofloxacin, ofloxacin, lomefloxacin, pefloxacin, rufloxacin, and sparfloxacin, including their pharmaceutically acceptable salts.

Representative compounds from the aminoglycoside class include, for example, tobramycin, amikacin, gentamicin, kanamycin, streptomycin, neomycin and netlimicin, including their pharmaceutically acceptable salts. Representative compounds from the macrolide class include erythromycin, clarithromycin, and azithromycin, including their pharmaceutically acceptable salts. Representative compounds from tetracycline class include tetracycline, oxytetracycline, doxycycline, and minocycline, including their pharmaceutically acceptable salts. Other antibacterial agents included in this invention are: IB-367 (Intrabiotics Pharm, Inc., Mountainview, Calif., USA), and daptomycin (Cubist Pharmaceuticals, Boston, USA) including their pharmaceutically acceptable salts.

The medicament of the present invention may additionally contain one or more co-therapeutic agents such as anti-inflammatory, bronchodilatory, antihistamine, decongestant or anti-tussive drug substances, for example as potentiators of therapeutic activity of such compounds of formula 1 or 2 or as a means of reducing required dosaging or potential side effects of such compounds of formula 1 or 2.

Active drug or therapeutic agents, when employed in combination with the compounds, or pharmaceutical compositions of the present invention, may be used or administered, for example, in dosage amounts Indicated in the Physicians' Desk Reference (PDR) or as otherwise determined by one of ordinary skill in the art.

In the context of this specification, the term "simultaneously" when referring to simultaneous administration of the relevant drugs means at exactly the same time, as would be the case, for example in embodiments where the drugs are combined in a single preparation. In other embodiments, "simultaneously" can mean one drug taken a short duration after another, wherein "a short duration" means a duration which allows the drugs to have their intended synergistic effect.

In light of the foregoing, the present invention also relates to a combination therapy, which may be a comprised of a simultaneous or co-administration, or serial administration of a combination of compounds or pharmaceutical compositions of the compounds of the present Invention with other active drug or therapeutic agents, such as described above, and where such administration also is determined by one of ordinary skill in the art.

in addition, the present invention also relates to a combination therapy for the treatment or prevention of a bacterial infection as described herein, which is comprised of a composition, dosage form or formulation formed from a synergistic combination or mixture of compounds, controlled release compositions, dosage forms or formulations of the present invention and another active drug or therapeutic agent or agents as those described above and optionally which comprises pharmaceutically acceptable carrier, diluent or adjuvant. In such an aforementioned combination composition, dosage form or formulation of the present invention, each of the active drug components are contained in therapeutically effective and synergistic dosage amounts. The Examples set forth below are illustrative of the present invention and are not intended to limit, in any way, the scope of the present invention.

Other Uses

The compounds described herein may also be used as part of an in vitro assay, for example, in order to determine whether a candidate host is likely to benefit from treatment with the compound in question.

The Compounds of formula 1 or 2 described herein may also be used as a standard, for example, in an assay, in order to identify other compounds, other anti-bacterial agents, etc.

Kits

One aspect of the invention pertains to a kit comprising (a) a compound of formula 1 or 2 as described herein, or a composition comprising a compound of formula 1 or 2 as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The compound of formula 1 or 2 or pharmaceutical composition comprising the a compound of formula 1 or 2 may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eyedrops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly. In one preferred embodiment, the route of administration is oral (e.g., by ingestion).

In one preferred embodiment, the route of administration is parenteral (e.g., by injection).

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

Formulations

While it is possible for the compound of formula 1 or 2 to be administered alone, it is preferable to present it as a pharmaceutical formulation (e.g., composition, preparation, medicament) comprising at least one compound of formula 1 or 2, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound of formula 1 or 2, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation. Suitable carriers, diluents, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 5th edition, 2005. The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof. Formulations may suitably be in the form of liquids, solutions (e.g., aqueous, nonaqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other micro particulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions {e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropyl methyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach. Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used. Formulations suitable for intranasal administration, where the carrier is a liquid, include, for example, nasal spray, nasal drops, or by aerosol administration by nebuliser, include aqueous or oily solutions of the compound. Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, dichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound. Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema. Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other micro particulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection.

Typically, the concentration of the compound in the liquid is from about 1 ng/mL to about 10 µg/mL, for example, from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use.

Extemporaneous injection solutions and suspensions may be prepared from sterile powders, granules, and tablets.

Dosage

It will be appreciated by one of skill in the art that appropriate dosages of the compounds of formula 1 or 2, and compositions comprising the compounds of formula 1 or 2, can vary from patient to patient. Determining the optimal dosage will generally involve the balancing of the level of therapeutic benefit against any risk or deleterious side effects. The selected dosage level will depend on a variety of factors including, but not limited to, the activity of the particular compound of formula 1 or 2, the route of administration, the time of administration, the rate of excretion of the compound of formula 1 or 2, the duration of the treatment, other drugs, compounds, and/or materials used in combination, the severity of the condition, and the species, sex, age, weight, condition, general health, and prior medical history of the patient. The amount of a compound of formula 1 or 2 and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician. In general, a suitable dose of the compound of formula 1 or 2 is in the range of about 50 µg to about 20 mg (more typically about 100 µg to about 10 mg) per kilogram body weight of the subject per day. Where the compound is a salt, an ester, an amide, a prodrug, or the like, the amount administered is calculated on the basis of the parent compound and so the actual weight to be used is increased proportionately.

Pharmaceutically acceptable salt or corresponding pharmaceutical compositions of the present invention have a wide antimicrobial activity spectrum, and may be used for prevention or therapy against a variety of diseases caused by causative bacteria In a variety of mammals including humans, for example, airway Infectious diseases, urinary system infectious diseases, respiratory system infectious diseases, sepsis, nephritis, cholecystitis, oral cavity infectious diseases, diphteria, endocarditis, pneumonia, bone marrow membrane myelitis, meningoencephalitis prostatitis, venereal infections, otitis media, enteritis, empyema, cutaneous infections, wound infectious diseases, opportunistic infection and the like.

Compounds of Formulas 1 or 2 or a pharmaceutically acceptable salt thereof and/or corresponding pharmaceutical compositions of the present invention exhibit high antimicrobial activity against Gram positive and Gram negative bacteria, preferably, Gram negative bacteria of enterobacteria (*E. coli, Klebsiella, Serrata, Enterobacter, Citrobacter, Morganella, Providencia, Proteus* and the like), Gram negative bacteria colonized in respiratory system (*Haemophilus, Moraxeila* and the like), Gram negative bacteria found in the environment (*Alcaligenes, Achromobacter, Burkholderia, Chryseobacterium* and the like) and Gram negative bacteria of glucose non fermentation (*Pseudomonas aeruginosa, Pseudomonas* other than *P. aeruginosa, Stenotrophomonas, Burkholderia, Acinetobacter* and the like. Gram positive bacteria include *Staphyloccocus* species, *Streptococcus* species, *Pneumococcus* species and *Bacillus* species.

In the present invention by "resistant" or "resistance" it is meant the ability of resist to antibacterial drugs or compounds currently on the market, in particular drugs belonging to the penicillin class (PEN), cephalosporin class (CEPH), expanded spectrum cephalosporin (ES-CEPH) carbapenem (CARB), Aztreonam (AZT), flouroquinolones (FQ), Fosfomycin (FOS), sulfamethoxazole/trimethoprim (SXT), Monobactam (MON), aminoglycosides (AG), glycopeptides (GLY), Linezolid (LNZ), colistin (COL). The terms also encompasses multi-resistant i.e poly-drug resistant (PDR).

In the present invention the following abbreviations are used:

THF: tetrahydrofuran; DCM: dichloromethane; EDC: 1-Ethyl-(3-dimethylaminopropyl)carbodiimide; $CH_3CN$: Acetonitrile; AcOEt: ethylacetate; TEA: triethylamine; DIPEA: diisopropylethylamine; MeOH: methanol; MeOD:

deuterated methanol; Cbz: Benzyloxy carbamate; TFA: trifluoroacetic acid; DMF: N,N-dimethylformamide; DMSO: dimethyl sulfoxide; r.t.: room temperature; h: hour(s); NMR: Nuclear Magnetic Resonance.

The following examples and biological data are presented in order to further illustrate the invention.

DETAILED DESCRIPTION OF THE INVENTION

Example 1: Chemistry

All commercially available chemicals were used as purchased. DCM was dried over sodium hydride. THF were dried over Na/benzophenone prior to use. Anhydrous DMF was used as purchased. Anhydrous reactions were run under a positive pressure of dry $N_2$ or argon.

Chromatographic separation of final products were conducted using a Polaris C18 column (150-4.6 mm, 5 μm particle size) at a flow rate of 0.8 mL min-1 with a mobile phase composed of 50% $CH_3CN$/50% $H_2O$-formic acid 0.1%.

Instrumentation $^1$H-NMR and $^{13}$C-NMR were measured on a 400 mHz spectrometer and are reported in parts per million (δ scale) and internally referenced to the $CDCl_3$ or $CD_3OD$ signal, respectively at δ 7.24 ppm and 3.31 ppm. Chemical shifts for carbon are reported in parts per million (δ scale) and referenced to the carbon resonances of the solvent ($CDCl_3$ at δ 77.00 and $CD_3OD$ at δ 49.00 ppm). Data is presented as follows: chemical shift, multiplicity (s=singlet, d=doublet, m=multiplet and/or multiplet resonances, br s=broad singlet), coupling constant in Hertz (Hz), and integration. Mass spectra (MS) data were acquired on an Agilent 1100 LC/MSD VL system (G1946C) with a 0.4 mL/min flow rate using a binary solvent system of 95:5 methanol/water. UV detection was monitored at 254 nm. Mass spectra were acquired in positive mode scanning over the mass range.

Compounds of general formula 1, when $R_2$, $R_4$, $R_6$, $R_8$ are H, L=0 and X is O, described in this invention can be synthesized as reported in Scheme 1 starting from triamine 3. The guanylation in steps "i" and "ii" can be conducted using an appropriate guanylating agent, preferably a N-substituted N,N'-di-Boc-S-methylisothiourea or a N-substituted N.N'-di-Boc-1H-pyrazolecarboxamidine. Linear intermediates 7a or 7b represent the key intermediates for the synthesis. Compound 7a-b can be prepared with different R groups ($R_1$, $R_2$, $R_3$, $R_4$) and with different n ($n_1$, $n_2$) and m ($m_1$, $m_2$) numbers.

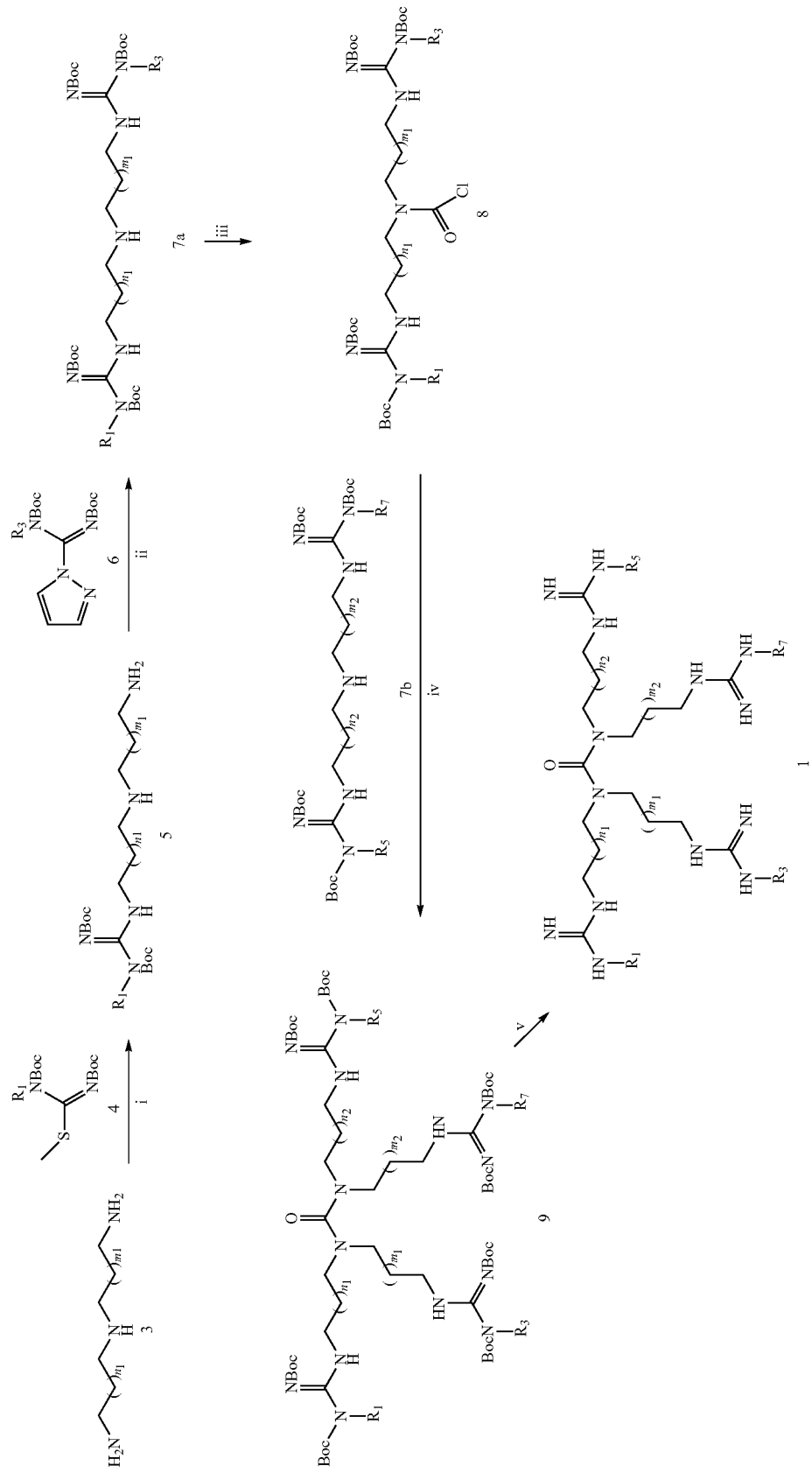
Scheme 1.
Reagents and conditions: (i) DIPEA, CH$_3$CN/MeOH, 50° C., 12-48 h; (ii) DIPEA, THF, 50° C., 12-48 h (iii) Triphosgene, DIPEA, THF, 0° C., 10 min; (iv) DIPEA, NaI, DCM, 40° C., 48 h; (v) TFA, DCM 8-24 h. In the scheme R$_1$, R$_3$, R$_5$, R$_7$, n$_2$, n$_1$, m$_1$ and m$_2$ are defined above.

The present invention provides also an alternative synthesis of compound 7a or 7b reported in scheme 2. This synthetic pathway is more complex but more versatile.

Scheme 2. Alternative synthesis of compound 7a or 7b:

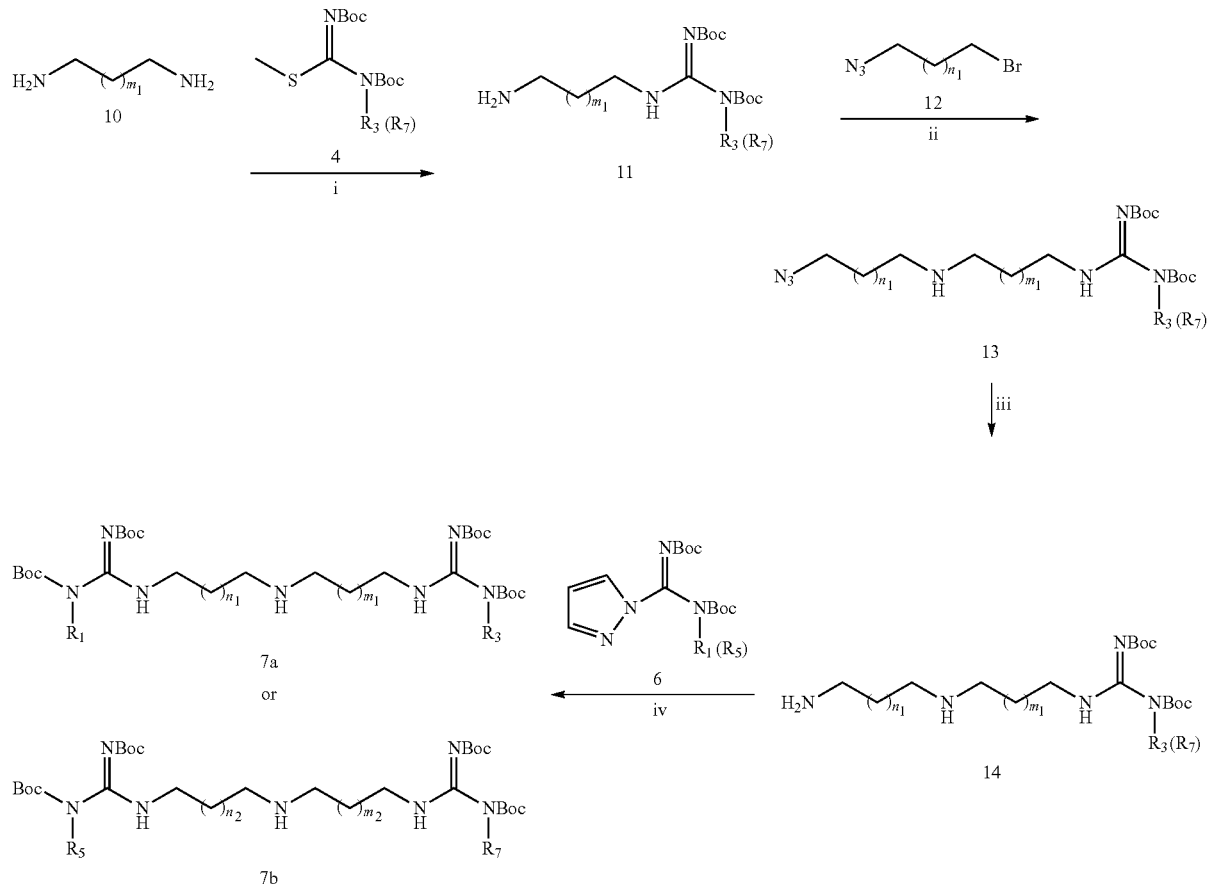

Reagents and conditions. (i) DIPEA, CH$_3$CN/MeOH, 50° C., 12-48 h; (ii) CsOH*H$_2$O, molecular sieves, DMF, r.t. 12 h; (iii) PPh$_3$, H$_2$O, THF, r.t., 12 h (iv) DIPEA, THF, 50° C., 12-48 h. In the scheme R$_1$, R$_3$, n$_1$, and m$_1$ are defined as above.

Compounds of general formula 2, when R$_2$, R$_4$, R$_6$, R$_8$ are H, described in this invention can be synthesized as reported in Scheme 3 starting from different or equal compounds of formula 7a-b.

Scheme 3.

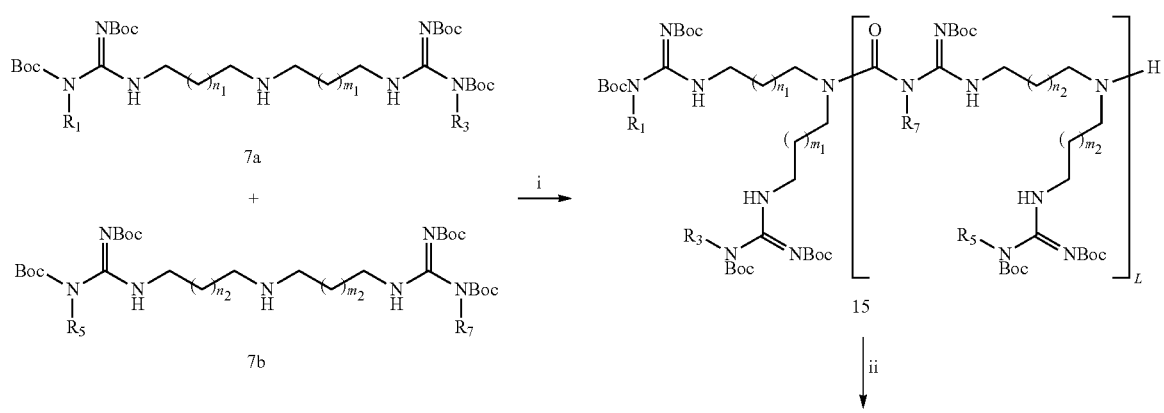

-continued

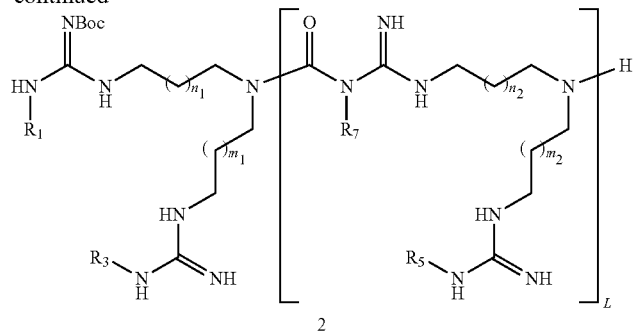

2

Reagents and conditions: (i) THF, reflux, 12-48 h; (ii) TFA, DCM, r.t., 8-24 h. In the scheme $R_1, R_3, R_3, R_7, n_1, n_2, m_1, m_2$ and L are defined as above. In step (i) by varying the concentration of compound 7a or 7b and the reflux time from 12 h to 48 h, products with an increasing nuber of L units can be synthesized and the reaction's status can be monitored through mass spectrometry.

In scheme 3 in step (i) by varying the concentration in the range from 50 to 300 mM and the reflux time from 5 h to 36 h, products with an increasing number of L units can be synthesized and the reaction's status can be monitored through mass spectrometry.

Depending on the synthetic strategy used in the last step the resulting compounds can be isolated as salts, such as trifluoroacetate salts.

In scheme 1-3 as a result of the last step, the cleavage of the Boc protecting group,—the compounds are obtained as trifluoroacetate salts, but the counterion can be changed if appropriate purification steps are applied, such as HPLC with acidified water.

The guanylating agents used for each synthesis have been obtained through Mitsunobu reaction between the desired alcohol and the tert-butyl N-[[(2-methylpropan-2-yl)oxycarbonylamino]-pyrazol-1-ylmethylidene]carbamate (Scheme 4).[9]

Scheme 4: Synthesis of guanylating compound 6.

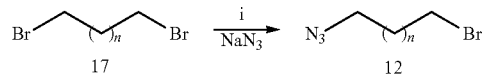

Reagent and conditions: DIAD, PPh$_3$, THF dry, 0° C., to reflux, 12 h

Compound 12 has been obtained by reacting the opportune linear dibromide with sodium azide using DMF as solvent. (Scheme 5)

Scheme 5: Synthesis of 17.

Br—(—)$_n$—Br  $\xrightarrow[\text{NaN}_3]{\text{i}}$  N$_3$—(—)$_n$—Br

17  →  12

Reagent and conditions: DMF, 50° C., 12 h.

Example 2: Synthesis of Representative Compound 28

Synthesis of Compound 28

Scheme 6.

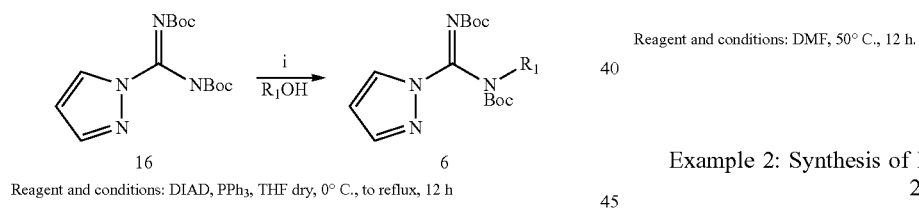

-continued

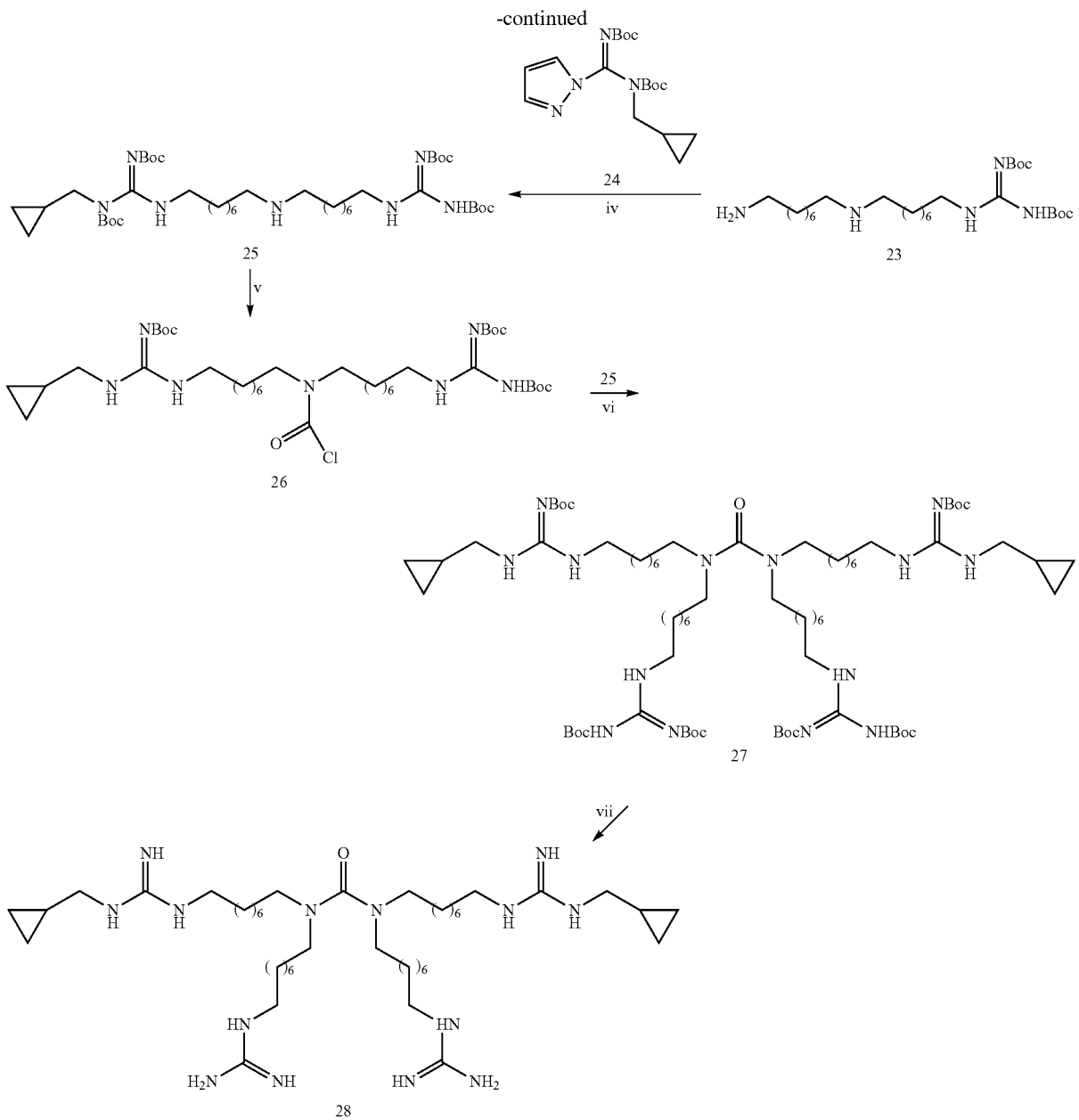

Reagents and conditions: (i) DIPEA, CH₃CN/MeOH, 50° C., 12 h; (ii) CsOH*H₂O, molecular sieves, DMF, r.t. 12 h; (iii) PPh₃, H₂O, THF; r.t., 12 h (iv) DIPEA, THF, 50° C., 12 h (v) Triphosgene, DIPEA, THF, 0° C., 10 min; (vi) DIPEA, NaI, DCM, 40° C., 48 h; (vii) TFA, DCM, r.t. 12 h Synthesis of Boc-Protected Guanidine 20:

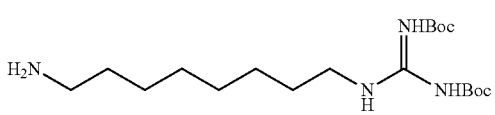

1,8-diaminooctane 18 (6.0 g, 41.67 mmol) was dissolved in half solution of CH₃CN/MeOH 9:1 (75.0 mL) and 1,3-Bis(tert-butoxycarbonyl)-2-methyl-2-thiopseudourea 19 (4.036 g, 13.89 mmol) in the other half (75.0 mL). The two solutions were mixed and the temperature was increased to 40-50° C. DIPEA (3.0 mL) was added to the reaction mixture and it was stirred 12 h. The reaction mixture was then concentrated and the crude product was purified by flash chromatography (CH₃CN/MeOH/Et₃N 8:2:1) to afford compound 20 as a pale yellow oil (yield 89%). $^1$H NMR (CDCl₃) δ (ppm): 1.30 (m, 12H); 1.49 (s, 18H); 2.67 (t, 2H, J=7.0 Hz); 3.40 (m, 2H); 8.28 (bs, 1H); 11.49 (bs, 1H). LCMS m/z (ES+)=387 [M+H]$^+$ Synthesis of 1-azido-8-bromooctane 21:

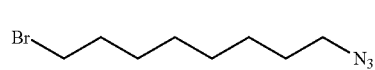

To a solution of dibromooctane (2.0 mL, 10.9 mmol) in DMF (2.0 mL), NaN₃ (354.3 mg, 5.45 mmol) was added and the reaction mixture was stirred 12 h at 50° C. After cooling, the reaction mixture was diluted with AcOEt. The organic phase was extracted twice with H₂O and then with Brine. The combined organic layers were dried over Na₂SO₄ and then evaporated. The crude product was purified with chromatography column in silica gel (eluent: Petroleum Ether) to afford compound 21 as a yellow oil (yield 82%). ¹H NMR (CDCl₃) δ (ppm): 1.33 (m, 6H); 1.43 (m, 2H); 1.60 (m, 2H); 1.85 (m, 2H); 3.25 (m, 2H); 3.40 (m, 2H).

Synthesis of azide 22:

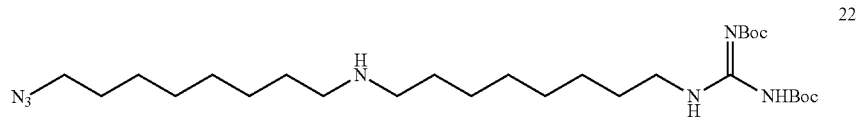

DMF dry (5.0 mL) and molecular sieves (600.0 mg), previously dried in oven, were inserted into a flask with a magnetic stirrer under N₂ atmosphere and stirred. CsOHxH₂O (266.0 mg, 1.585 mmol) was added and the mixture was stirred for 10 minutes. Then, a solution of 20 (612.0 mg, 1.585 mmol) in DMF dry was added and the mixture was stirred for further 30 minutes. Then, compound 21(297.0 mg, 1.268 mmol) was added and the reaction mixture was stirred 12 h. The mixture was diluted with AcOEt, filtered from the solid, washed and concentrated. The residue was treated with NaOH 1N and extracted with AcOEt. The organic phase was washed with H₂O, LiCl 5% and Brine. The crude product was purified with chromatography column in silica gel (eluent: DCM/MeOH 95:5; 9:1; 8:2) to afford compound 22 with a yield of 43%. ¹H NMR (CDCl₃) δ (ppm): 1.25 (m, 24H); 1.44 (s, 18H); 2.52 (t, 4H, J=7.0 Hz); 3.19 (t, 2H, J=6.8 Hz); 3.34 (q, 2H, J=5.6 Hz); 8.23 (bs, 1H); 11.50 (bs, 1H). ¹³C NMR (CDCl₃) δ (ppm): 26.53, 26.68, 27.18, 27.95, 28.70, 28.96, 29.07, 30.01, 40.84, 49.98, 51.34, 53.31, 79.03, 82.84, 153.22, 155.98, 163.55. LCMS m/z (ES+)=540.1 [M+H]⁺

Synthesis of Primary Amine 23

Compound 22 (341.1 mg, 0.63 mmol) was dissolved in THF (13.5 mL);

Triphenilphosphine (246.3 mg, 0.94 mmol) was added and the reaction mixture was stirred at room temperature for 30 minutes, monitoring the level of starting material. Then, H₂O (170.0 μL, 9.45 mmol) was added and the mixture was stirred 12 h. H₂O and AcOEt were added to the reaction mixture and the organic phase was washed with H₂O and Brine. The crude product was purified with a silica gel column chromatography (DCM/MeOH 9:1, DCM/MeOH 8:2, DCM/MeOH/Et₃N 8:2:1), affording compound 23 with a yield of 91%. ¹H NMR (MeOD) δ (ppm): 1.35 (m, 24H); 1.52 (s, 18H); 2.62 (t, 4H, J=7.6 Hz); 3.30 (m, 2H); 3.39 (m, 2H). LCMS m/z (ES+)=514.2 [M+H]⁺

Synthesis of tert-butyl (((tert-butoxycarbonyl)imino)(1H-pyrazol-1-yl)methyl) (cyclopropylmethyl)carbamate 24

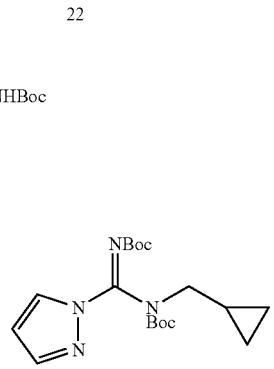

N,N'-Di-Boc-1H-pyrazole-1-carboxamidine (500.0 mg, 1.61 mmol) was dissolved in THF dry (6.2 mL). Then Triphenylphosphine (631.4 mg, 2.41 mmol) and Hydroxymethyl-cyclopropane (150.5 mg, 2.09 mmol) were added. The reaction mixture was cooled at 0° C. and Diisoporpyl azodicarboxylate (0.47 mL, 2.41 mmol) was added dropwise. The temperature was increased to 70° C. and the reaction mixture was stirred at reflux 12 h. The reaction mixture was concentrated and then diluted with DCM and H₂O. The aqueous phase was extracted for three times with DCM; the organic phases were collected, washed with brine twice and dried over Na₂SO₄. Solvent was removed in vacuum. The crude product was purified with chromatography column in silica gel (eluent: Petroleum Ether/AcOEt

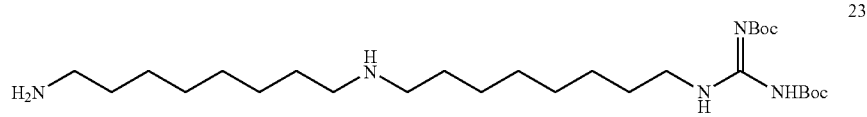

9:1) to afford compound 24 as a yellow oil (yield 82%). ¹H NMR (CDCl₃) δ (ppm): 0.45 (d, 2H, J=4.8 Hz); 0.49 (d, 2H, J=5.6 Hz); 1.27 (s, 9H); 1.49 (s, 9H); 1.54 (s, 1H); 3.60 (d, 2H, J=6.8 Hz); 6.41 (t, 1H, J=2.2 Hz); 7.69 (d, 1H, J=1.2 Hz); 7.95 (s, 1H). LCMS m/z (ES+)=387.1 [M+Na]⁺

Synthesis of Protected Diguanidine 25

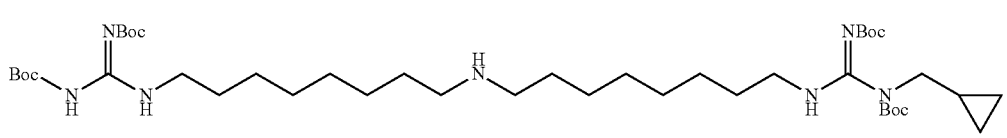

A solution of compound 24 (262.1 mg, 0.72 mmol) in THF (5.8 mL) was added to compound 23. DIPEA (0.1 mL, 0.60 mmol) was added and the reaction mixture was stirred 12 h at room temperature. Then, the mixture was diluted with AcOEt and washed with NaHCO₃, water and Brine. The combined organic layers were dried over Na₂SO₄ and concentrated. The crude product was purified with a silica gel column chromatography (DCM/MeOH 9:1), affording compound 25 with a yield of 70%. $^1$H NMR (CDCl₃) δ (ppm): 0.24 (d, 2H, J=4.8 Hz); 0.45 (d, 2H, J=7.6 Hz); 1.04 (m, 1H); 1.31 (m, 24H); 1.49 (s, 36H); 2.58 (t, 4H; J=7.2 Hz); 3.30 (m, 2H); 3.39 (q, 2H, J=6.5 Hz); 3.53 (m, 2H); 8.28 (bs, 1H). $^{13}$C NMR (CDCl₃) δ (ppm): 3.44, 10.48, 26.80, 27.17, 28.16, 28.85, 29.08, 29.71, 40.85, 43.79, 49.77, 52.06, 79.05, 81.76, 82.86, 153.22, 155.98, 163.54. LCMS m/z (ES+)=810.3 [M+H]⁺

Synthesis of Carbamoyl Chloride 26

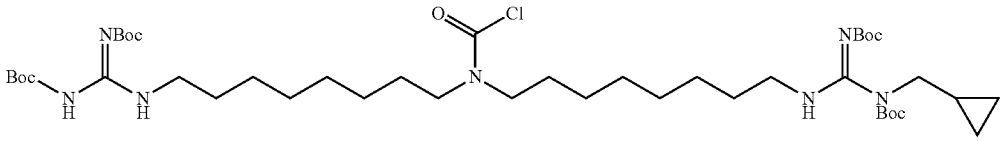

Compound 25 (42.4 mg, 0.05 mmol) was dissolved in THF dry (1.0 mL) and stirred under nitrogen atmosphere. The reaction mixture was cooled to 0° C. and DIPEA (9.0 µL, 0.05 mmol) and Triphosgene (14.9 mg, 0.05 mmol) were added. The mixture was stirred 10 minutes at 0° C. and then at room temperature for 1 h. Then, AcOEt and NaHCO₃ (s.s.) were added to the reaction mixture and it was stirred for 10 minutes. The aqueous phase was extracted twice with AcOEt and the combined organic layers were dried over Na₂SO₄ and concentrated. The crude product was purified with a silica gel column chromatography (DCM/MeOH 98:2), affording compound 26 with a yield of 72%. $^1$H NMR (CDCl₃) δ (ppm): 0.24 (d, 2H, J=4.8 Hz); 0.44 (d, 2H, J=8.0 Hz); 0.86 (m, 2H); 1.31 (s, 16H); 1.49 (s, 36H); 1.59 (s, 8H); 3.30 (m, 4H); 3.36 (m, 4H); 3.54 (m, 2H); 8.27 (bs, 1H); 11.49 (bs, 1H). $^{13}$C NMR (CDCl₃) δ (ppm): 3.47, 10.50, 26.05, 26.66, 27.38, 27.99, 28.15, 28.22, 28.84, 29.04, 29.58, 40.81, 43.78, 49.82, 51.12, 79.11, 82.92, 153.11, 156.01, 162.55. LCMS m/z (ES+)=872.2 [M+H]⁺; 436.5 [M+2H]²⁺

Synthesis of Urea 27

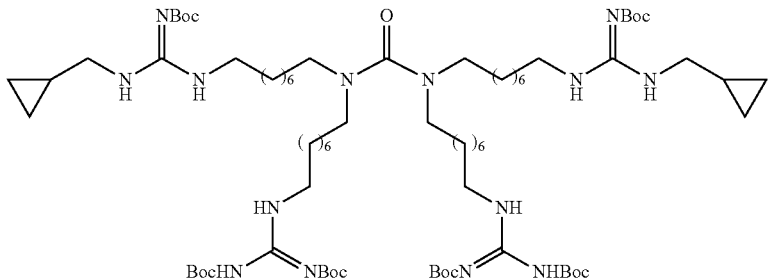

Compounds 25 (42.1 mg, 0.052 mmol) and 26 (31.0 mg, 0.035 mmol) were dissolved in DCM dry (3.0 mL). DIPEA (6.0 µL, 0.035 mmol) and NaI (catalytic) were added and the reaction mixture was stirred 12 h at 35-40° C. After cooling, AcOEt, NaOH 1N and water were added to the reaction mixture and it was stirred for 10 minutes. The aqueous phase was extracted three times with AcOEt and the combined organic layers were dried over Na₂SO₄ and concentrated. The crude product was purified with a silica gel column chromatography (EP/AcOEt 8:2), affording compound 27 with a yield of 60%. $^1$H NMR (CDCl₃) δ (ppm): 0.26 (d, 4H, J=4.8 Hz); 0.43 (d, 4H, J=7.6 Hz); 1.03 (m, 2H); 1.29 (m, 48H); 1.48 (s, 72H); 3.05 (m, 8H); 3.28 (m, 4H); 3.38 (m, 4H); 3.53 (m, 4H); 8.28 (bs, 2H); 11.49 (bs, 2H). LCMS m/z (ES+)=823.5 [M+2H]²⁺; 549.4 [M+3H]³⁺

Synthesis of Final Compound 28

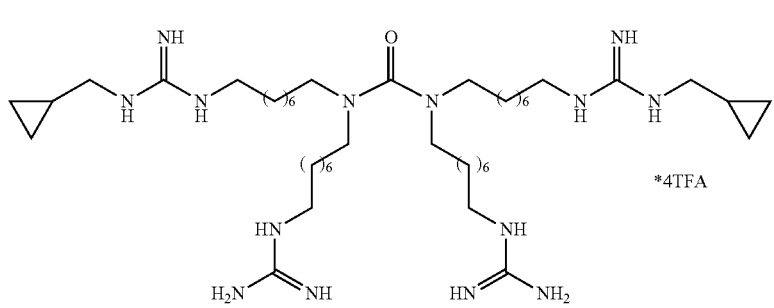

Compound 27 (12.5 mg, 7.6×10⁻³ mmol) was dissolved in DCM dry (1.8 mL) and TFA 10% (0.2 mL) was added. The reaction mixture was stirred at room temperature for 7.5 h. Then the solvent was evaporated and compound 28 was obtained in quantitative without any further purification as trifluoroacetate salt. $^1$H NMR (MeOD) δ (ppm): 0.26 (d, 4H, J=4.8 Hz); 0.58 (d, 4H, J=7.2 Hz); 1.05 (m, 2H); 1.34 (m, 24H); 3.05 (d, 4H, J=6.8 Hz); 3.15 (m, 16H). $^{13}$C NMR (CDCl$_3$) δ (ppm): 2.39, 9.53, 26.17, 26.54, 27.51, 28.36, 28.45, 28.83, 28.93, 40.97, 41.09, 45.78, 46.87, 47.08, 47.30, 156.32, 158.66, 165.23. LCMS m/z (ES+)=845.0 [M+H]$^+$; 423.3 [M+2H]$^{2+}$; 282.5 [M+3H]$^{3+}$; 212.1 [M+4H]$^{4+}$

Example 3: Synthesis of Representative Compound 30

Synthesis of Compound 30

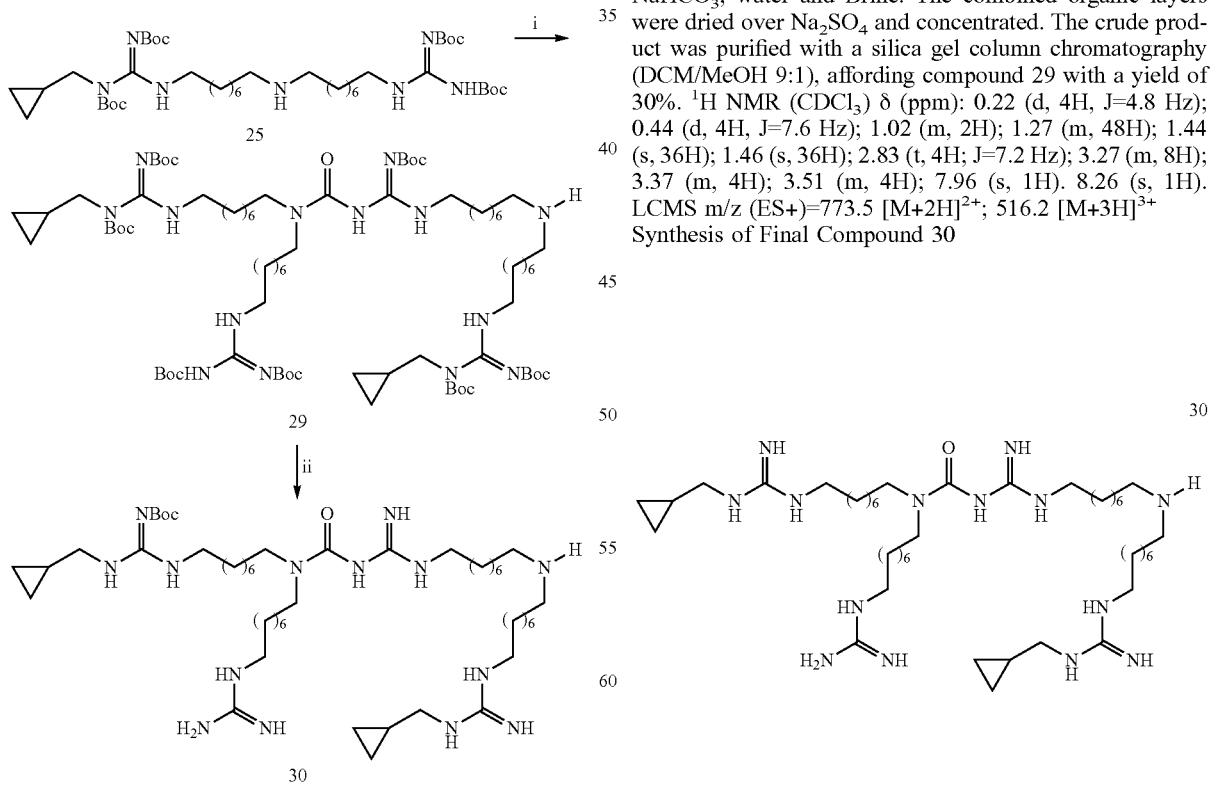

Reagents and conditions: (i) THF, reflux, 12 h; (ii) TFA, DCM, r.t., 12 h.

Synthesis of Primary Amine 29

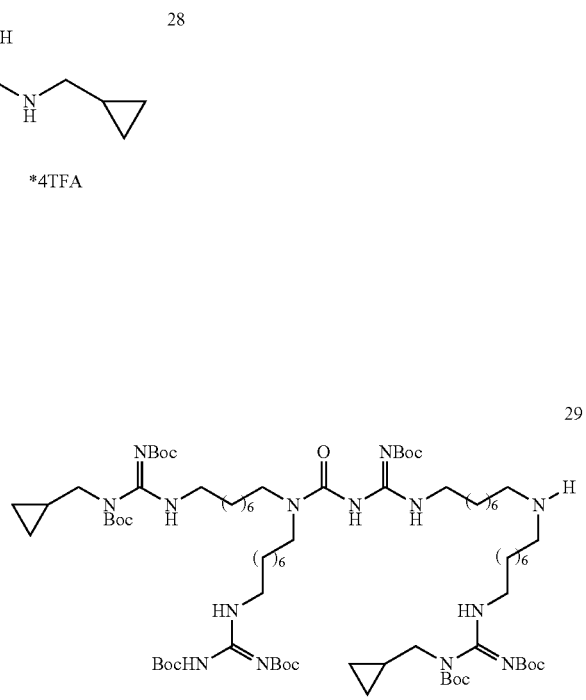

A 100 millimolar solution in dry THF of compound 25 (54.3 mg, 0.07 mmol) was heated at reflux for 12 h. Then, the mixture was diluted with AcOEt and washed with NaHCO$_3$, water and Brine. The combined organic layers were dried over Na$_2$SO$_4$ and concentrated. The crude product was purified with a silica gel column chromatography (DCM/MeOH 9:1), affording compound 29 with a yield of 30%. $^1$H NMR (CDCl$_3$) δ (ppm): 0.22 (d, 4H, J=4.8 Hz); 0.44 (d, 4H, J=7.6 Hz); 1.02 (m, 2H); 1.27 (m, 48H); 1.44 (s, 36H); 1.46 (s, 36H); 2.83 (t, 4H, J=7.2 Hz); 3.27 (m, 8H); 3.37 (m, 4H); 3.51 (m, 4H); 7.96 (s, 1H). 8.26 (s, 1H). LCMS m/z (ES+)=773.5 [M+2H]$^{2+}$; 516.2 [M+3H]$^{3+}$ Synthesis of Final Compound 30

Compound 29 (17.2 mg, 0.01 mmol) was dissolved in DCM dry (1.8 mL) and TFA 10% (0.2 mL) was added. The reaction mixture was stirred at room temperature for 10 h.

Then the solvent was evaporated and compound 30 was obtained in quantitative without any further purification as trifluoroacetate salt. $^1$H NMR (MeOD) δ (ppm): 0.24 (d, 4H, J=5.2 Hz); 0.56 (d, 4H, J=7.6 Hz); 1.04 (m, 2H); 1.26-1.33 (m, 36H); 1.45-1.55 (m, 12H); 2.52 (t, 4H, J=7.2 Hz); 3.04 (d, 4H, J=6.8 Hz) 3.11-3.17 (m, 12H), 3.32 (s, 4H). 2.43, 9.88, 26.17, 26.54, 27.33, 28.38, 28.77, 28.93, 40.31, 41.19, 45.89, 47.28, 47.31, 156.21, 158.70, 164.77, 168.22. LCMS m/z (ES+)=845.0 [M+H]$^+$; 423.3 [M+2H]$^{2+}$; 282.5 [M+3H]$^{3+}$; 212.1 [M+4H]$^{4+}$

TABLE 1

Synthesized compounds

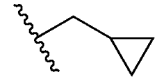 [SMILES: *CC1CC1]

1

| | L | X | $n_{(1-3)}$ | $m_{(1-3)}$ | $R_1$ | $R_2$, $R_4$, $R_6$, $R_8$, $R_{10}$ $R_{12}$ applicable) | $R_3$, $R_7$ ($R_{11}$ if applicable) | $R_5$ ($R_9$ if applicable) |
|---|---|---|---|---|---|---|---|---|
| Compound 31 | 0 | O | 4 | 4 | 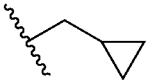 | H | H | 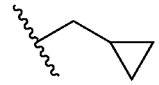 |
| Compound 28 | 0 | O | 6 | 6 | 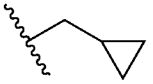 | H | H | 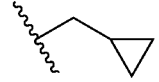 [SMILES: *CC1CC1] |
| Compound 32 | 1 | O | 6 | 6 | 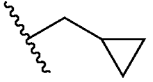 [SMILES: *CC1CC1] | H | H | 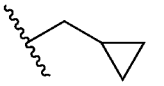 |

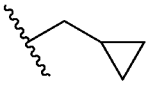

2

| | L | $n_{(1-2)}$ | $m_{(1-2)}$ | $R_1$ | $R_2$, $R_3$, $R_4$, $R_6$, $R_8$, | $R_3$, $R_7$ | $R_5$ |
|---|---|---|---|---|---|---|---|
| Compound 33 | 1 | 4 | 4 | | H | H | |
| Compound 30 | 1 | 6 | 6 | | H | H | |
| Compound 34 | 2 | 4 | 4 | | H | H | |

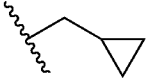 [SMILES: *CC1CC1]

TABLE 1-continued

| Compound 35 | 2 | 6 | 6 |  | H | H |  |

All the compounds have been tested as trifluoroacetate salts.

Example 4: Antimicrobial Susceptibility Testing

Methods

Bacterial strains were obtained from the ATCC or CCUG culture collections or present in the authors' collection of clinical isolates [10]. Compounds were re-suspended in dimethyl sulfoxyde (DMSO) at a final concentration of 10 mg/ml and subsequently diluted in the culture medium. The minimum inhibitory concentrations (MICs) of the compounds of the invention were determined using the microdilution broth method using Mueller-Hinton broth as recommended by the Clinical Laboratory Standards Institute (CLSI [11]). Bacterial inoculum was $5 \times 10^4$ CFU/well. MICs were recorded after 18-24 hours incubation at 35-37° C.

Results

Results of the antimicrobial susceptibility assays are shown in Table 2. Compound 28, belonging to formula 1, bearing a cyclopropylmethyl group as substituent $R_1$ and $R_5$ and zero repeating units (L is 0), seems to be the most active among the series. Although most of the compounds showed a higher antimicrobial activity against Gram-positive bacteria, compounds 28 and partially compound 32 show the broadest antimicrobial spectrum, and result active against both Gram-positive and Gram-negative organisms, especially clinically relevant Enterobacteriaceae, i.e. *Escherichia coli* and *Klebsiella pneumonia*.

TABLE 2

Biological results of five tested compounds

| | Compound MIC (µg/ml) | | | | |
|---|---|---|---|---|---|
| Bacterial strain | 31 | 28 | 32 | 33 | 30 |
| *Achromobacter xylosoxidans* AX 22 | >256 | 8 | 64 | >256 | >256 |
| *Acinetobacter baumannii* ATCC 17978 | 128 | 4 | 32 | 256 | >256 |
| *Alcaligenes faecalis* 424/98 | >256 | 8 | 32 | >256 | 32 |
| *Burkholderia cepacia* RII | >256 | 8 | 128 | >256 | 128 |
| *Chryseobacterium meningosepticum* CCUG 4310 | >256 | 64 | 64 | >256 | >256 |
| *Escherichia coli* CCUG$^T$ | 16 | 1 | 8 | 32 | >256 |
| *Klebsiella pneumoniae* ATCC 13833 | 32 | 1 | 8 | 64 | >256 |
| *Pseudomonas aeruginosa* ATCC 27853 | 256 | 4 | 32 | >256 | >256 |
| *Stenotrophomonas maltophilia* 634/08 | >256 | 16 | 64 | >256 | >256 |
| *Bacillus subtilis* ATCC 6633 | 4 | 0.5 | 8 | 8 | <0.125 |
| *Enterococcus faecalis* ATCC 19433 | 32 | <0.125 | <0.125 | 32 | 8 |
| *Staphylococcus aureus* ATCC 25923 | 4 | 2 | 8 | 16 | 4 |
| *Acinetobacter baumannii* AC-54/97 (IMP-2) | — | 2 | 16 | 8 | 32 |
| *Enterobacter cloacae* VA-417/02 (VIM-4) | — | 1 | 16 | 64 | — |
| *Klebsiella pneumoniae* 081R | — | 2 | 16 | — | — |

MIC = Minimal Inhibitory Concentration

TABLE 3

Bactericidal activity of compound 28

| | Compound 28 | |
|---|---|---|
| Bacterial strain | MIC µg/ml | MBC µg/ml |
| *Achromobacter xylosoxidans* AX 22 | 8 | 8 |
| *Acinetobacter baumannii* ATCC 17978 | 4 | 4 |
| *Alcaligenes faecalis* 424/98 | 8 | 8 |
| *Burkholderia cepacia* RII | 8 | 8 |
| *Chryseobacterium meningosepticum* CCUG 4310 | 64 | 64 |
| *Escherichia coli* CCUG$^T$ | 1 | 1 |
| *Klebsiella pneumoniae* ATCC 13833 | 1 | 1 |
| *Pseudomonas aeruginosa* ATCC 27853 | 4 | 4 |
| *Stenotrophomonas maltophilia* 634/08 | 16 | 16 |
| *Bacillus subtilis* ATCC 6633 | 0.5 | 0.5 |
| *Enterococcus faecalis* ATCC 19433 | <0.125 | <0.125 |
| *Staphylococcus aureus* ATCC 25923 | 2 | 2 |
| *Acinetobacter baumannii* AC-54/97 (IMP-2) | 2 | 2 |
| *Enterobacter cloacae* VA-417/02 (VIM-4) | 1 | 1 |
| *Klebsiella pneumoniae* 081R | 2 | 2 |

MIC = Minimal Inhibitory Concentration;
MBC = Minimal Bactericidal Concentration The Antibacterial activity of compound 28 was also tested on a panel of Gram-negative and Gram-positive clinical isolates, showing various antimicrobial susceptibility profiles (Table 4). The class of drugs for which the isolate was resistant to is indicated in column 2 (PEN, penicillins; ES-CEPH, expanded-spectrum cephalosporins; CARB, carbapenems; AZT; aztreonam; AG, aminoglycosides; FQ, fluoroquinolones; SXT, trimethoprim/sulfamethoxazole; FOS, fosfomycin; GLY, glycopeptides; LNZ, linezolid; COL-R, colistin resistant; COL-S colistin sensitive; PDR, poly-drug resistant).

Example 5: In Depth Biological Evaluation of Compound 28

The biological profile of compound 28 which was the most active of the series was further investigated by evaluating the bactericidal activity (Table 3) as well as the activity against selected resistant strains (Table 4).

TABLE 4

Biological activity of compound 28 against a selected panel of resistant pathogens

| Bacterial Strain | Resistance Profile | Comp 28 MIC (µg/ml) |
|---|---|---|
| GRAM-NEGATIVES | | |
| Acinetobacter baumannii AC-54/97 | PEN, ES-CEPH, CARB, AZT, AG, FQ, FOS, SXT | 4 |
| Enterobacter cloacae VA-417/02 | PEN, CEPH, CARB, AG, FQ | 2 |
| Klebsiella pneumoniae 7023 | PEN, ES-CEPH, CARB, AG, FQ, SXT | 2 |
| Klebsiella pneumoniae KP0787 | PDR | 1 |
| Pseudomonas aeruginosa 101/1477 | PEN, ES-CEPH, CARB, AG | 8 |
| Pseudomonas aeruginosa VR143/97 | PEN, ES-CEPH, CARB, MON, AG, FQ | 8 |
| Pseudomonas aeruginosa 14X-34 | PDR | 8 |
| Klebsiella pneumoniae BO1 | COL-S | 4 |
| Klebsiella pneumoniae BO4 | COL-R | 8 |
| Klebsiella pneumoniae B1 | COL-S | 4 |
| Klebsiella pneumoniae B2 | COL-R | 4 |
| Klebsiella pneumoniae 207-1 | COL-S | 4 |
| Klebsiella pneumoniae 207-2 | COL-R | 8 |
| Klebsiella pneumoniae 081R | PDR | 4 |
| Klebsiella pneumoniae 167R | PDR | 4 |
| GRAM-POSITIVES | | |
| Staphylococcus aureus ATCC 43300 (MRSA) | PEN | 4 |
| Staphylococcus aureus ATCC 700699 (VanA) | GLY | 4 |
| Staphylococcus haemolyticus SI-6/2011 | AG | 2 |
| Staphylococcus warneri SI-5/2011 | PEN, AG | 2 |

Example 6: ADME Properties of Compound 28

In vitro ADME properties (apparent permeability in gastrointestinal model, microsomal stability and binding to plasma proteins) for compound 28 were evaluated.

Parallel Artificial Membrane Permeability Assay

Method

Donor solution (0.5 mM) was prepared by diluting 1 mM dimethylsulfoxide (DMSO) compound stock solution using tris-HCl buffer (50 mM) at pH 7.4. Filters were coated with 5 µL of a 1% (w/v) dodecane solution of phosphatidylcholine. Donor solution (150 µL) was added to each well of the filter plate. To each well of the acceptor plate were added 300 µL of solution (50% DMSO in phosphate buffer). Compound 28 was tested in three different plates on different days. The sandwich was incubated for 5 h at room temperature under gentle shaking. After the incubation time, the plates were separated, and samples were taken from both receiver and donor sides and analyzed using LC with UV detection at 210 and 254 nm. LC analysis were performed with a Perkin-Elmer (series 200) instrument equipped with an UV detector (Perkin-Elmer 785A, UV/vis Detector). Chromatographic separation were conducted using a Polaris C18 column (150-4.6 mm, 5 µm particle size) at a flow rate of 0.8 mL min-1 with a mobile phase composed of 50% $CH_3CN$/50% $H_2O$-formic acid 0.1%.

Permeability (Papp) was calculated according to equation 1, obtained from Sugano [12] and Wohnsland [13] equation with some modification to obtain values in cm/s.

$$P_{app} = \frac{V_D V_A}{(V_D + V_A)At} - \ln(1-r) \quad (1)$$

Where $V_A$ is the volume in the acceptor well, $V_D$ is the volume in the donor well ($cm^3$), A is the effective area of the membrane ($cm^2$), t is the incubation time (s) and r the ratio between drug concentration in the acceptor and equilibrium concentration of the drug in the total volume ($V_D+V_A$). Drug concentration was estimated by using the peak area integration.

Results

The apparent permeability ($P_{app}$) was measured by using the Parallel Artificial Membrane Permeability Assay (PAMPA), at pH 7.4. PAMPA assays on compound 28 revealed a low permeability value ($1.6 \times 10^{-6}$ cm/s) at physiological pH.

Metabolic Stability Assay

Methods

Compound 28 in DMSO solution was incubated at 37° C. for 60 min in 50 mM Tris-HCl buffer (pH 7.4), 5 µL of human liver microsomal proteins (0.2 mg $mL^{-1}$), in the presence of a NADPH-generating system at a final volume of 0.5 mL (compounds' final concentration, 50 µM); DMSO did not exceed 2% (final solution). The reaction was stopped by cooling in ice and adding 1.0 mL of acetonitrile. The reaction mixtures were then centrifuged, and the parent drug and metabolites were subsequently determined by LC-UV-MS as reported for the solubility assay Results Metabolic stability of compound 28 was measured on human liver microsomial enzymes. Compound 28 showed a very good metabolic stability (99.9% in 1 h of incubation at 37° C.).

Binding Fluorimetric Assay

Methods

A quantitative analysis of the potential interaction was performed by fluorimetric titration: 0.2 mL. solution, containing a fixed concentration of HSA (10 µM in phosphate buffer 1 mM), was titrated with different amounts of 28, Carbamazepine and Paracetamol (2 µM to 2500 µM by stock solutions in DMSO). The solutions were mixed and after allowing 30 minutes at room temperature to reach the equilibrium conditions, the spectra were recorded. All fluorescence studies were done at room temperature, Tryptophan fluorescence emission spectra over 250-500 nm wavelength range were recorded with excitation wavelength set at 290 and the emission peaks of HAS were observed at 340 nm. 28 analyzed by the fluorimetric titration, showed decrease of intrinsic fluorescence of Tryptophan and the percentage of bound albumin at various concentrations, was calculated. The percentages obtained were plotted against the concentrations used and the $K_D$ values were calculated using GraphPad software (version 5.0).

Results

Quenching of the intrinsic Tryptophan of Human Serum Albumin (HAS) was monitored by fluorescence spectroscopy in order to determine the dissociation constant ($K_D$) with compound 28 to HAS. Paracetamole and Carbamazepine were used for comparison. When a fixed concentration of HSA was titrated with different amounts of our compound, a scarce intrinsic fluorescence decrease was observed. [14] The experimental results suggest that 28 as similar behaviour to paracetamol. [15] On the contrary, carbamazepine shows a remarkable intrinsic fluorescence decrease. [16]

FIG. 1 shows binding curves for Carbamazepine, Paracetamol and 28. Calculated experimental Kd values are:
for compound 28 >400 µM
PARACETAMOL >400 µM
CARBAMAZEPINE 102.4±19.7 µM.

Water Solubility

Methods

Solid compound 28 (1.01 mg) was added to 1 mL of water. The sample was shaken in a shaker bath at room temperature for 24 h. The suspension was filtered through a 0.45-µm nylon filter (Acrodisc), and the solubilised compound determined by LC-UV-MS assay. The determination was performed in triplicate. For the quantification was used an LC-UV-MS system consisted of a Varian apparatus (Varian Inc) including a vacuum solvent degassing unit, two pumps (212-LC), a Triple Quadrupole MSD (Mod. 320-LC) mass spectrometer with ES interface and Varian MS Workstation System Control Vers. 6.9 software. Chromatographic separation was obtained using a Pursuit C18 column (50×2.0 mm) (Varian) with 3 µm particle size and gradient elution: eluent A being CH3CN and eluent B consisting of an aqueous solution of formic acid (0.1%).

The analysis started with 0% of eluent A, which was linearly increased up to 50% in 10 min, then slowly increased up to 60% up to 15 min. The flow rate was 0.4 ml/min and injection volume was 20 µL. The instrument operated in positive mode and parameters were: detector 1850 V, drying gas pressure 25.0 psi, desolvation temperature 300.0° C., nebulizing gas 45.0 psi, needle 5000 V and shield 600 V. Nitrogen was used as nebulizer and drying gas. Collision induced dissociation was performed using Argon as the collision gas at a pressure of 1.8 mTorr in the collision cell, the collision energy was set to 149 eV. UV lamp was set to 210 nm. Calibration curve was obtained by analysing standard methanolic solution of compound 28 at serial dilutions. The calculation was based on the integral value of the UV peak at 14.6 min retention time.

Results

The water solubility of compound 28 was also determined by LC-UV-MS analysis, using the calibration curve method. Experimental solubility value found is 292 µg/mL.

REFERENCES

[1] Theuretzbacher, U. *Int. J. Antimicrob. Agents.* 2012 39(4):295-299
[2] Frazee, B. W.; et al., *Ann. Emerg. Med.* 2005, 45 (3), 311-20
[3] Manetti, F., et al. *J. Med. Chem.* 2009, 52(23), 7376-7379
[5] Berge, S. M. et al., *J. Pharm. Sci.* 1977, 66, 1-19
[6] Gould, P. L. *Int. J. Pharm* 1986, 33, 201-217
[7] Bighley et al. *Encyclopedia Of Pharmaceutical Technology*, Marcel Dekker Inc, New York 1996, Volume 13, 453-497
[8] Remington: "The Science and Practice of Pharmacy", Lippincott Williams & Wilkins, 2000.
[9] Mitsunobu, O.; Yamada, M. Bull. *Chem. Soc. Jpn.* 1967, 40, 2380
[10] Riccio, M. L.; et al. *Antimicrob. Agents Chemother.* 2001, 45(4), 1249-1253
[11] Clinical Laboratory Standards Institute. M07-A9: Methods for Dilution Antimicrobial Susceptibility Tests for Bacteria That Grow Aerobically; Approved Standard—Ninth Edition. 2012. Clinical Laboratory Standards Institut, Wayne, Pa.
[12] Sugano, K.; Hamada, H.; Machida, M.; Ushio, H. *J. Biomol. Screen.* 2001, 6, 189
[13] Wohnsland, F.; Faller, B. *J. Med. Chem.* 2001, 44, 923
[14] Zhang, G, et al. *Spectrochim Acta A Mol Biomol Spectrosc* 2010, 410-417
[15] Parikh, H. H., et al. *Pharm Res* 2000, 632-637
[16] Kim, H. S., Mallik, M., Hage, D. S. *J. Chromatography B* 2006, 138-146

The invention claimed is:

1. A compound of general formula 1:

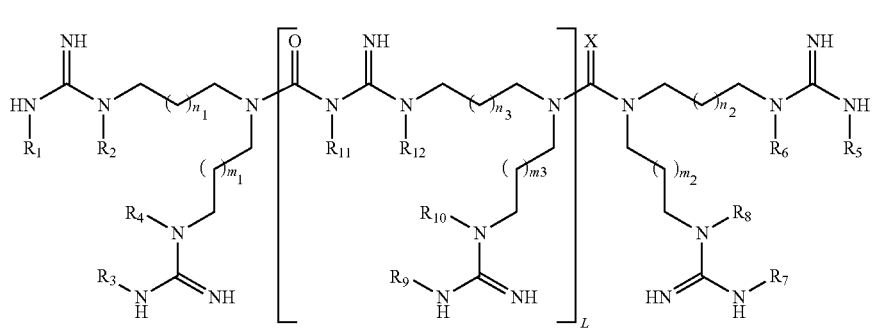

or a pharmaceutical acceptable salt, hydrate or solvate thereof;

wherein:

$R_1$, $R_3$, $R_5$, $R_7$, $R_9$ and $R_{11}$ are the same or different groups, selected from the group consisting of H, methyl, ethyl, propyl, prop-2-ynyl, but-2-enyl, 2-methylprop-2-enyl, 3-methylbut-2-enyl, phenyl, benzyl, dimethylphenyl, cyclopropylmethyl, cyclobutylmethyl, cyclopentylmethyl, cyclohexylmethyl, acetyl, propanoyl, N-alkyl-carbamoyl, N-alkyl-thiocarbamoyl, N-alkyl-carbamimidoyle and saturated linear or branched $C_{1-10}$ alkyl;

$R_2$, $R_4$, $R_6$, $R_8$, $R_{10}$ and $R_{12}$ are the same or different groups, selected from the group consisting of H, methyl, ethyl, and saturated linear or branched $C_{1-5}$ alkyl;

X is O or S;

L is a number from 0 to 2;

$n_1$, $n_2$ and $n_3$ can be the same or different and are numbers from 2 to 10; and $m_1$, $m_2$ and $m_3$ can be the same or different and are numbers from 2 to 10.

2. The compound according to claim 1 wherein L=0.

3. The compound according to claim 1 wherein $n_1=n_2=m_1=m_2=6$.

4. The compound according to claim 1 wherein $R_1$ and/or $R_5$ is cyclopropylmethyl.

5. The compound according to claim 1 wherein $R_1$ and/or $R_5$ is ethyl, benzyl, propargyl or but-2-enyl.

6. The compound according to claim 1 being selected from the group consisting of:
 1,3-bis(6-(3-(cyclopropylmethyl)guanidino)hexyl)-1,3-bis(6-guanidinohexyl)urea-3-;
 1,3-bis(8-(3-(cyclopropylmethyl)guanidino)octyl)-1,3-bis(8-guanidinooctyl)urea;
 1,3-bis(8-(3-(cyclopropylmethyl)guanidino)octyl)-1-(8-guanidinooctyl)-3-(8-((3-(8-((8-(3-(cyclopropylmethyl))guanidinooctyl)amino)octyl)carbamoyl)guanidino)octyl)urea;
 1,3-bis(8-(3-(ethyl)guanidino)octyl)-1,3-bis(8-guanidinooctyl)urea;
 1,3-bis(8-(3-(buten-2-yl)guanidino)octyl)-1,3-bis(8-guanidinooctyl)urea;
 1,3-bis(8-(3-(benzyl)guanidino)octyl)-1,3-bis(8-guanidinooctyl)urea;
 1,3-bis(8-(3-(propargyl)guanidino)octyl)-1,3-bis(8-guanidinooctyl)urea;
 1,3-bis(9-(3-(cyclopropylmethyl)guanidino)nonyl)-1,3-bis(9-guanidinononyl)urea;
 1,3-bis(9-(3-(ethyl)guanidino)nonyl)-1,3-bis(9-guanidinononyl)urea;
 1,3-bis(9-(3-(buten-2-yl)guanidino)nonyl)-1,3-bis(9-guanidinononyl)urea;
 1,3-bis(9-(3-(benzyl)guanidino)nonyl)-1,3-bis(9-guanidinononyl)urea;
 1,3-bis(9-(3-(propargyl)guanidino)nonyl)-1,3-bis(9-guanidinononyl)urea;
 1,3-bis(10-(3-(cyclopropylmethyl)guanidino)decyl)-1,3-bis(10-guanidinodecyl)urea;
 1,3-bis(10-(3-(ethyl)guanidino)decyl)-1,3-bis(10-guanidinodecyl)urea;
 1,3-bis(10-(3-(buten-2-yl)guanidino)decyl)-1,3-bis(10-guanidinodecyl)urea;
 1,3-bis(10-(3-(benzyl)guanidino)decyl)-1,3-bis(10-guanidinodecyl)urea; and
 1,3-bis(10-(3-(propargyl)guanidino)decyl)-1,3-bis(10-guanidinodecyl)urea.

7. A compound having the general formula 2:

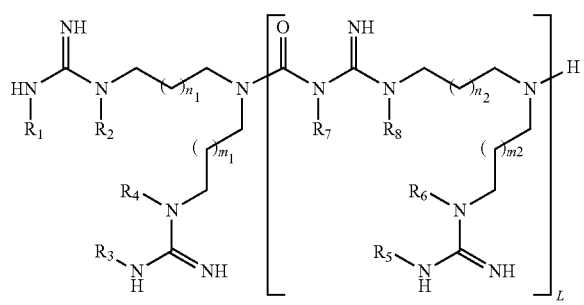

or a pharmaceutical acceptable salt, hydrate or solvate thereof;

wherein:
 $R_1$, $R_3$, $R_5$, and $R_7$, are the same or different groups, selected from the group consisting of H, methyl, ethyl, propyl, prop-2-ynyl, but-2-enyl, 2-methylprop-2-enyl, 3-methylbut-2-enyl, phenyl, benzyl, dimethylphenyl, cyclopropylmethyl, cyclobutylmethyl, cyclopentylmethyl, cyclohexylmethyl, acetyl, propanoyl, N-alkyl-carbamoyl, N-alkyl-thiocarbamoyl, N-alkyl-carbamimidoyl and saturated linear or branched $C_{1-10}$ alkyl;
 $R_2$, $R_4$, $R_6$, and $R_5$, are the same or different groups, selected from the group consisting of H, methyl, ethyl, and saturated linear or branched $C_{1-5}$ alkyl
 L is a number from 1 to 3;
 $n_1$ and $n_2$ can be the same or different and are numbers from 2 to 10; and
 $m_1$ and $m_2$ can be the same or different and are numbers from 2 to 10.

8. The compound according to claim 7 wherein L=1.

9. The compound according to claim 7 wherein $R_1$ and/or $R_5$ is cyclopropylmethyl.

10. The compound according to claim 7 being selected from the group consisting of:
 1-(6-carbamimidamidohexyl)-1-[6-[[N-(cyclopropylmethyl)carbamimidoyl]amino]hexyl]-3-[N-[6-[6-[[N cyclopropylmethyl)carbamimidoyl]amino]hexylamino]hexyl]carbamimidoyl]urea;
 1-(8-carbamimidamidooctyl)-1-[8-[[N-(cyclopropylmethyl)carbamimidoyl]amino]octyl]-3-[N-[8-[8-[[N-(cyclopropylmethyl)carbamimidoyl]amino]octylamino]octyl] carbamimidoyl]urea;
 1-(6-carbamimidamidohexyl)-1-[6-[[N-(cyclopropylmethyl)carbamimidoyl]amino]hexyl]-3-[N-[6-[6-[[N-(cyclopropylmethyl)carbamimidoyl]amino]hexyl-[[N-[6-[6-[[N-(cyclopropylmethyl) carbamimidoyl]amino]hexylamino]hexyl]carbamimidoyl]carbamoyl]amino]hexyl]carbamimidoyl]urea; and
 1-(8-carbamimidamidooctyl)-1-[8-[[N-(cyclopropylmethyl)carbamimidoyl]amino]octyl]-3-[N-[8-[8-[[N-(cyclopropylmethyl)carbamimidoyl]amino]octyl-[[N-[8-[8-[[N-(cyclopropylmethyl) carbamimidoyl]amino]octylamino]octyl]carbamimidoyl]carbamoyl]amino]octyl]carbamimidoyl]urea.

11. A method for the treatment of a bacterial infection comprising administering a compound of claim 1 to a patient in need thereof.

12. The method according to claim 11 wherein the bacteria is Gram-positive or Gram-negative.

13. The method according to claim 12 wherein the bacteria is selected from the group consisting of: *Enterococci, Staphylococci, Klebsiella* spp., *Acinetobacter* spp., *Pseudomonas* spp., *Enterobacter* spp., *Achromobacter* spp., *Aeromonas* spp., *Alcaligenes* spp., *Burkholderia cepacia, Chryseobacterium meningosepticum, Escherichia coli, Stenotrophomonas maltophilia* and *Bacillus subtilis*.

14. The method according to claim 11 wherein the bacteria is resistant to at least one antibiotic/antibacterial agent.

15. A pharmaceutical composition comprising a compound according to claim 1 or a pharmaceutical acceptable salt or solvate thereof and acceptable carriers, excipients or diluents.

16. The pharmaceutical composition according to claim 15 further comprising at least one other therapeutic agent.

17. A process for the preparation of a compound of formula 1 as defined in claim 1 comprising:

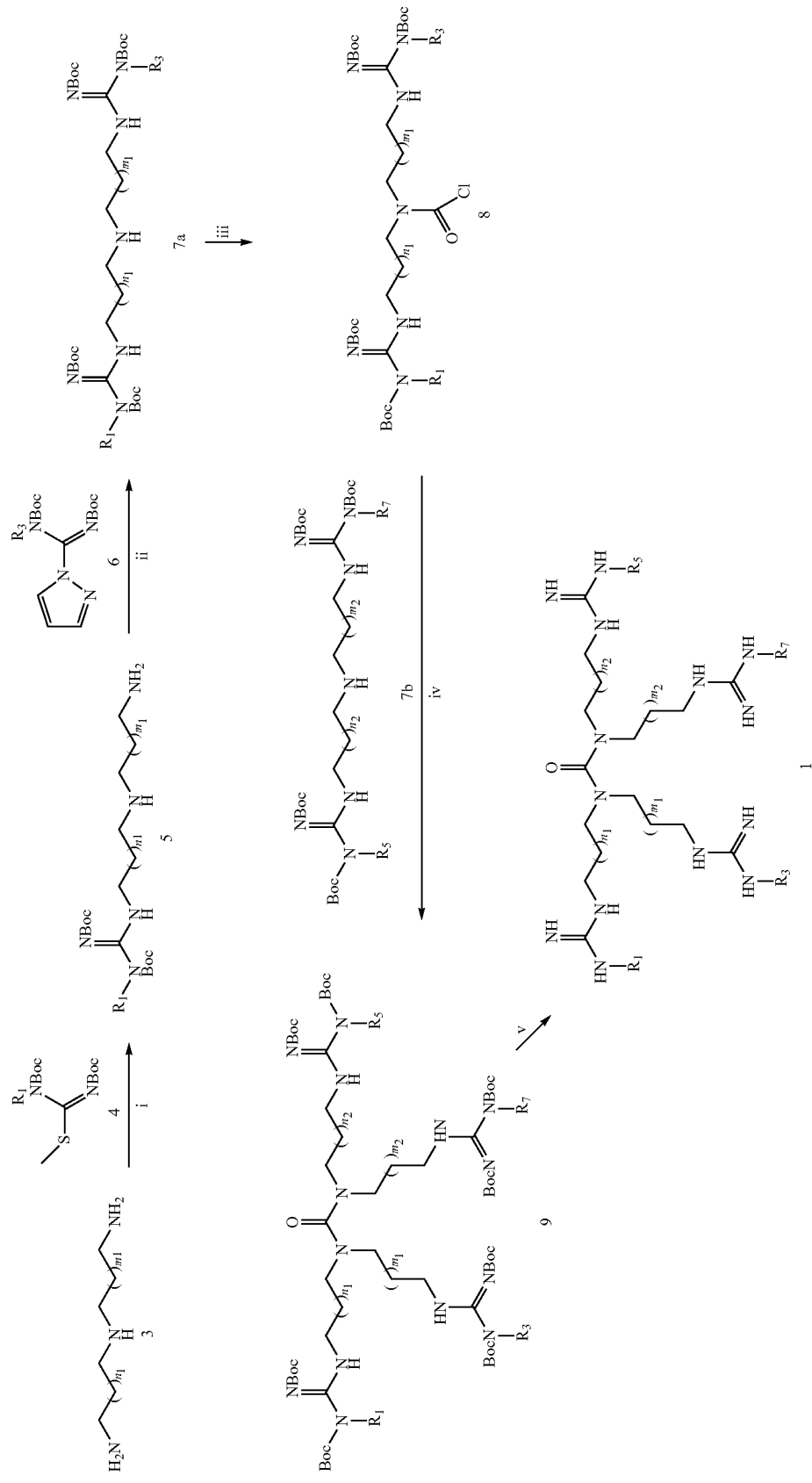

18. A process for the preparation of a compound of formula 2 as defined in claim 7 comprising:

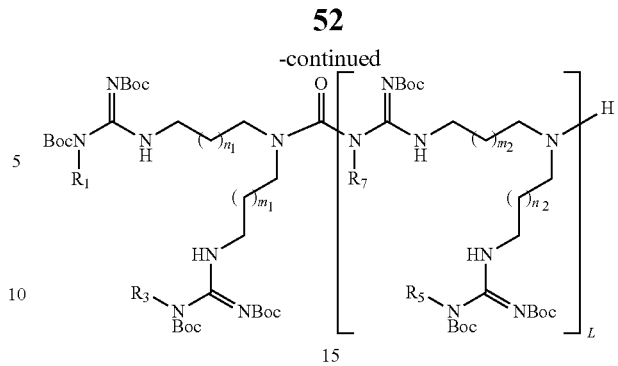

Scheme 3.

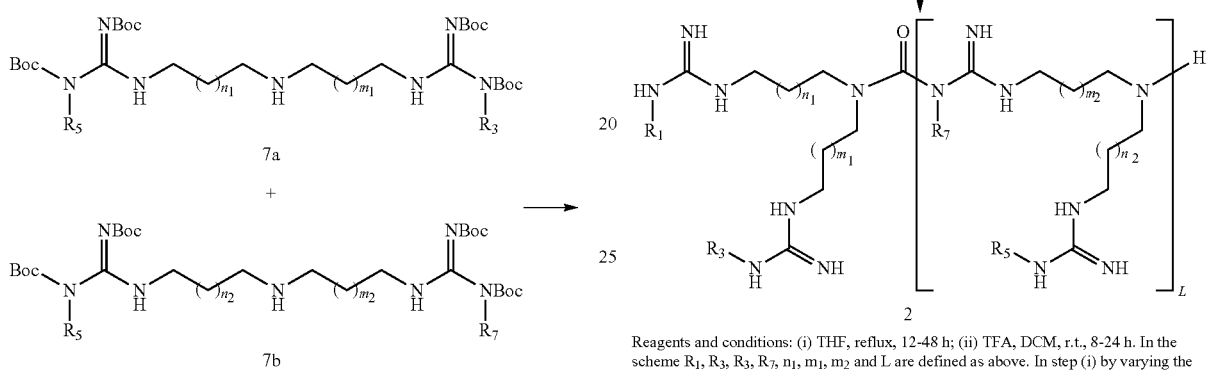

Reagents and conditions: (i) THF, reflux, 12-48 h; (ii) TFA, DCM, r.t., 8-24 h. In the scheme $R_1$, $R_3$, $R_3$, $R_7$, $n_1$, $m_1$, $m_2$ and L are defined as above. In step (i) by varying the concentration of compound 7a or 7b and the reflux time from 12 h to 48 h, products with an increasing number of L units can be synthesized and the reaction's status can be monitored through mass spectrometry.

19. A process for the preparation of an intermediate of formula 7a or 7b comprising:

Scheme 2. Alternative synthesis of compound 7a or 7b:

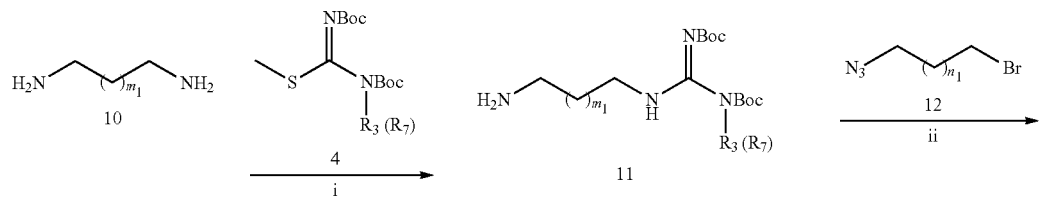

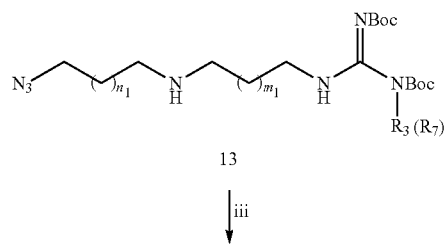

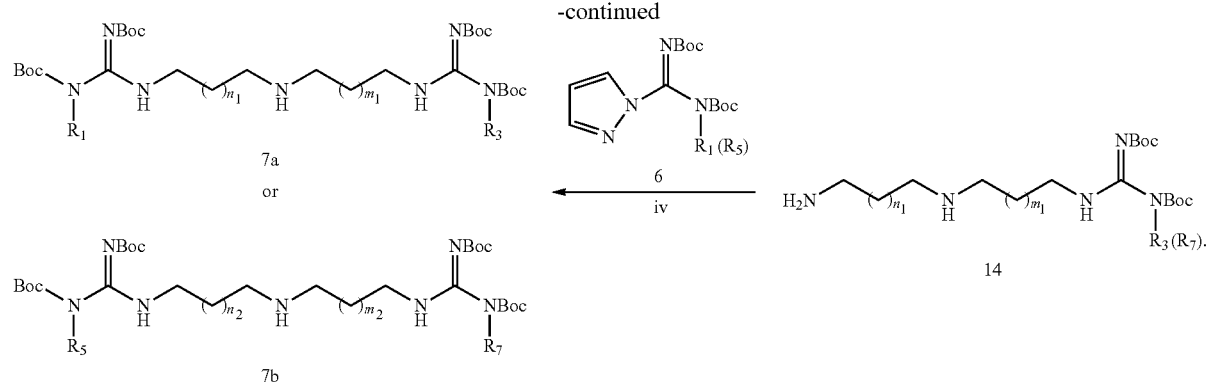

Reagents and conditions. (i) DIPEA, CH$_3$CN/MeOH, 50° C., 12-48 h; (ii) CsOH*H$_2$O, molecular sieves, DMF, r.t. 12 h; (iii) PPh$_3$, H$_2$O, THF, r.t., 12 h (iv) DIPEA, THF, 50° C., 12-48 h. In the scheme R$_1$, R$_3$, n$_1$, and m$_1$ are defined as above.

20. The process of claim 18, further comprising varying the concentration of compound 7a or 7b and the reflux time from 12 h to 48 h in order to produce compounds of formula 2 with an increasing number of L units.

\* \* \* \* \*